US007376836B2

(12) United States Patent
Graves et al.

(10) Patent No.: US 7,376,836 B2
(45) Date of Patent: May 20, 2008

(54) SYSTEMS AND METHODS FOR PREVENTING AN ATTACK ON HEALTHCARE DATA PROCESSING RESOURCES IN A HOSPITAL INFORMATION SYSTEM

(75) Inventors: Alan Frank Graves, Kanata (CA); Jeffrey Fitchett, Kanata (CA); Stephen Elliott, Allen, TX (US); John Watkins, Ottawa (CA); Dany Sylvain, Gatineau (CA)

(73) Assignee: Nortel Networks Limited, St-Laurent, Quebec (CA)

( * ) Notice: Subject to any disclaimer, the term of this patent is extended or adjusted under 35 U.S.C. 154(b) by 664 days.

(21) Appl. No.: 10/819,349

(22) Filed: Apr. 7, 2004

(65) Prior Publication Data

US 2005/0066061 A1   Mar. 24, 2005

Related U.S. Application Data

(60) Provisional application No. 60/505,941, filed on Sep. 25, 2003, provisional application No. 60/503,965, filed on Sep. 19, 2003.

(51) Int. Cl.
*H04L 9/00* (2006.01)
*H04L 9/32* (2006.01)
*G06F 15/16* (2006.01)
*G06F 17/30* (2006.01)
*G06F 9/00* (2006.01)
*H04N 7/16* (2006.01)

(52) U.S. Cl. .......................... 713/168; 713/153; 726/3; 726/12; 726/28

(58) Field of Classification Search ................ 713/153, 713/168; 726/12, 28, 3
See application file for complete search history.

(56) References Cited

U.S. PATENT DOCUMENTS

| 5,291,399 | A | 3/1994 | Chaco |
| 5,465,082 | A | 11/1995 | Chaco |
| 5,594,786 | A | 1/1997 | Chaco et al. |
| 5,677,952 | A | 10/1997 | Blakley, III et al. |
| 5,689,229 | A | 11/1997 | Chaco et al. |
| 5,818,939 | A | 10/1998 | Davis |
| 5,822,544 | A | 10/1998 | Chaco et al. |

(Continued)

OTHER PUBLICATIONS

Maiwald, Eric. Network Security A Beginner's Guide, Feb. 2001 Osborne/McGraw-Hill, pp. 133-165.*

(Continued)

*Primary Examiner*—Kambiz Zand
*Assistant Examiner*—Michael J Simitoski

(57) ABSTRACT

A system comprising a switching entity disposed between healthcare data processing resources and non-healthcare data processing resources. The switching entity is capable of operation in a first state in which an end user device is communicatively coupled to the healthcare data processing resources to support a healthcare session and a second state in which the end user device is communicatively coupled to the non-healthcare data processing resources to support a non-healthcare session. If the authentication request message is received while the switching entity is operating in the second state and a particular non-healthcare session is in progress, and the selected authentication entity is the healthcare authentication entity, initiating a memory purge at the end user device. Attacks on the healthcare data processing resources, both from the non-healthcare resources directly and via the end user device, are thus prevented.

75 Claims, 15 Drawing Sheets

U.S. PATENT DOCUMENTS

| | | | |
|---|---|---|---|
| 5,867,821 A * | 2/1999 | Ballantyne et al. | 705/2 |
| 5,933,136 A * | 8/1999 | Brown | 715/741 |
| 6,009,333 A | 12/1999 | Chaco | |
| 6,259,355 B1 | 7/2001 | Chaco et al. | |
| RE37,531 E | 1/2002 | Chaco et al. | |
| 6,344,794 B1 | 2/2002 | Ulrich et al. | |
| 6,462,656 B2 | 10/2002 | Ulrich et al. | |
| 6,539,393 B1 | 3/2003 | Kabala | |
| 6,825,763 B2 | 11/2004 | Ulrich et al. | |
| 6,876,303 B2 | 4/2005 | Reeder et al. | |
| 6,958,706 B2 | 10/2005 | Chaco et al. | |
| 6,963,979 B2 | 11/2005 | Fairclough et al. | |
| 6,972,683 B2 | 12/2005 | Lestienne et al. | |
| 6,993,661 B1 | 1/2006 | Garfinkel | |
| 7,038,588 B2 * | 5/2006 | Boone et al. | 340/573.1 |
| 7,042,337 B2 | 5/2006 | Borders et al. | |
| 7,080,061 B2 | 7/2006 | Kabala | |
| 7,120,139 B1 | 10/2006 | Kung et al. | |
| 7,154,397 B2 | 12/2006 | Zerhusen et al. | |
| 7,162,731 B2 | 1/2007 | Reidhead et al. | |
| 2002/0026105 A1 | 2/2002 | Drazen | |
| 2002/0032582 A1* | 3/2002 | Feeney et al. | 705/2 |
| 2002/0044059 A1 | 4/2002 | Reeder et al. | |
| 2002/0111831 A1* | 8/2002 | Harada | 705/3 |
| 2002/0183979 A1 | 12/2002 | Wildman | |
| 2002/0188466 A1* | 12/2002 | Barrette et al. | 705/2 |
| 2003/0014283 A1* | 1/2003 | Iwano et al. | 705/3 |
| 2003/0037247 A1 | 2/2003 | Obara et al. | |
| 2003/0065626 A1* | 4/2003 | Allen | 705/76 |
| 2003/0115447 A1 | 6/2003 | Pham et al. | |
| 2003/0132845 A1 | 7/2003 | McDaniel, III | |
| 2003/0165128 A1 | 9/2003 | Sisodia et al. | |
| 2003/0179223 A1 | 9/2003 | Ying et al. | |
| 2003/0208382 A1 | 11/2003 | Westfall | |
| 2004/0004968 A1 | 1/2004 | Nassar | |
| 2004/0068421 A1* | 4/2004 | Drapeau et al. | 705/2 |
| 2004/0193449 A1 | 9/2004 | Wildman et al. | |
| 2004/0260577 A1* | 12/2004 | Dahlin et al. | 705/2 |
| 2005/0035862 A1 | 2/2005 | Wildman et al. | |
| 2005/0063420 A1 | 3/2005 | Graves | |
| 2005/0086079 A1 | 4/2005 | Graves et al. | |
| 2005/0151641 A1 | 7/2005 | Ulrich et al. | |
| 2005/0168341 A1 | 8/2005 | Reeder et al. | |
| 2005/0223222 A1 | 10/2005 | Graves et al. | |
| 2005/0246553 A1 | 11/2005 | Nakamura et al. | |
| 2005/0272275 A1 | 12/2005 | Graves | |
| 2006/0282459 A1 | 12/2006 | Kabala | |

OTHER PUBLICATIONS

Clinical Decision Support, Finding The Right Path; by Jane Metzge, Donna Stablein and Fran Turisco; First Consulting Group; Sep. 2002.

Computerized Physician Order Entry, A Look at the Vendor Marketplace and Getting Started; by Jane Metzger and Fran Turisco; First Consulting Group; Dec. 2001.

Leapfrog Patient Safety Standards; The Potential Benefits of Universal Adoption, by J.D. Birkmeyer, The Leapfrog Group, Nov. 2000.

Computerized Physician Order Entry; Cost, Benefits and Challenges; A case study approach, by First Consulting Group for Advancing Health in America and the Federation of America Hospitals, Jan. 2003.

A Primer on Physician Order Entry; First Consulting Group for the California Healthcare Foundation, Oakland, CA, Sep. 2000.

Cisco Long-Reach Ethernet Solution; Product Catalog, Dec. 2003; (pp. 1-6).

Cisco Long-Reach Ethernet Frequently Asked Questions; downloaded from www.cisco.com as early as Feb. 13, 2004.

Cisco LRE/VDSL (Long-Reach Ethernet/Very-High-Data-Rate DSL); downloaded from www.cisco.com as early as Feb. 13, 2004.

Cisco LRE CPE Hardware Installation Guide, totaling 106 pages, text part No. 78-11469-04, May 2003.

Physician Adoption of Technology Linked to Providing Benefits; Technology and Quality; by Barry P. Chaiken, MD, MPH; Reprinted with permission from the Journal of Quality Health Care, vol. 1 Issue No. 2; Apr./Jun. 2002.

Microsoft Corporation, Microsoft TechNet, Data Protection Implementing the Encrypting File System in Windows 2000, 15 pages.

Jeff Schmidt, Microsoft Windows 2000 Security Handbook, Aug. 2000, 13 pages, Que Corporation.

Bruce Schneier, Applied Cryptography, 1996, 6 pages, John Wiley & Sons, Inc.

Chris Lawler, Taking a look at the basis of ASICs, Dec. 7, 1998, 2 pages, Copyright Network World Inc.

Ron White, How Computers Work, Oct. 2006, 8 pages, Que Corporation.

\* cited by examiner

SYSTEMS AND METHODS FOR PREVENTING AN ATTACK ON HEALTHCARE DATA PROCESSING RESOURCES IN A HOSPITAL INFORMATION SYSTEM

CROSS-REFERENCES TO RELATED APPLICATIONS

The present application claims the benefit under 35 USC §119(e) of U.S. provisional patent application Ser. No. 60/503,965 to Graves, filed Sep. 19, 2003, incorporated by reference herein and U.S. provisional patent application Ser. No. 60/505,941 to Graves, filed Sep. 25, 2003, incorporated by reference herein.

The present application claims the benefit under 35 USC §120 of the U.S. patent application Ser. No. 10/813,230 entitled "Integrated And Secure Architecture For Delivery Of Communications Services In A Hospital" to Graves et al., filed Mar. 31, 2004, incorporated by reference herein and the U.S. patent application Ser. No. 10/813,358 entitled "Systems And Methods For Preserving Confidentiality Of Healthcare Information In A Point-Of-Care Communications Environment" to Graves et al., filed Mar. 31, 2004, incorporated by reference herein.

FIELD OF THE INVENTION

The present invention relates generally to communications architectures and, in particular, to systems and methods for preventing an attack on healthcare data processing resources in a hospital information system. Such attacks arise, for example, when a patient intends to misuse the Internet for the purposes of hacking into medical records stored by the hospital information system, which can be a problem in a joint-use Point-Of-Care/Patient Entertainment System, as an example.

BACKGROUND OF THE INVENTION

The ability for healthcare users to interact with a hospital information system while at the point of care (POC), e.g., at a patient's bedside, is recognized as having the potential to dramatically reduce the incidence of certain medical complications. Specifically, studies estimate that significant benefits are likely to arise through the provision of "computerized physician order entry" (CPOE), which consists of allowing healthcare users (e.g., doctors, nurses, orderlies) to place orders (e.g., prescription, blood test, clean towel, etc.) via a bedside location in the vicinity of the patient being treated. This simple yet elusive paradigm, dubbed "CPOE at the POC", has the potential effect of reducing human error due to temporary memory loss and mistakes in transcription. In addition, when coupled with real-time decision information support tools (DIST), CPOE provides healthcare users with an additional level of assurance that their diagnosis or treatment plan falls within generally accepted parameters.

For background reading on the CPOE-at-the-POC paradigm and its predicted impact, the reader is referred to the following references, hereby incorporated by reference herein:

Clinical Decision Support—Finding the Right Path, by J. Metzger, D. Stablein and F. Turisco, First Consulting Group, September 2002

Computerized Physician Order Entry: Costs, Benefits and Challenges—A case Study Approach, by First Consulting Group for Advancing Health in America and the Federation of American Hospitals, January 2003

Leapfrog Patient Safety Standards—The Potential Benefits of Universal Adoption, by J. D. Birkmeyer, The Leapfrog Group, November 2000

Computerized Physician Order Entry: A Look at the Vendor Marketplace and Getting Started, by J. Metzger, F. Turisco, First Consulting Group, December 2001

A Primer on Physician Order Entry, by First Consulting Group for the California Healthcare Foundation, Oakland, Calif., September 2000

A typical example of a conventional CPOE-at-the-POC solution consists of a plurality of CPOE terminals with associated clinical software residing on those terminals, and which can access, read and input directly into the hospital information system infrastructure. All required healthcare information is downloaded to the terminal and written to the hard drive for use by the applications that are resident in the terminal. The terminals have gated access via an authentication, authorization and accounting (AAA) solution, based upon centralized authentication of user identity and authorization of that user to specific sets of privileges. By virtue of the fact that all of the healthcare applications are resident in the terminal, the terminal is typically to be a powerful workstation or personal computer (PC).

It is a reality, however, that healthcare institutions have neither sufficient funds nor adequate physical space to deploy customized CPOE terminals based on powerful processors, and containing healthcare applications and healthcare data for each patient at that patient's bedside. Recognizing that television terminals delivering patient entertainment services are to be found in virtually every patient room, and that TV display technology and PC display technology and image processing are in many cases converging, it has been proposed to make healthcare applications such as CPOE accessible to healthcare users via the same terminal that supplies the patient entertainment services. Thus, terminals and software have been developed, which allow both healthcare communications services and non-healthcare communications services to be accessed via a common user interface, albeit with significantly different authentication metrics.

One approach to reducing the requirement to deploy separate CPOE terminals lies in combining the healthcare and non-healthcare data delivery infrastructures at a common terminal. Some current systems which have adopted this approach provide healthcare applications (such as CPOE) for healthcare users, as well as health information, hospital information and entertainment/communication for non-healthcare users, via a common terminal and interface being fed by two underlying delivery infrastructures.

A problem with such conventional approaches is the lack of security arising from the dual-purpose nature of the common terminal. In particular, there exists the potential threat of a patient or outsider downloading so-called spyware (i.e., malicious software), AAA message collection software or other system-penetration software via non-healthcare sources (such as the Internet), and using the software so downloaded to attack the security or operation of the healthcare applications in the hospital information system. Clearly, this is a major consideration in the overall clinical system security and affects the degree to which healthcare providers will approve of delivering both healthcare and non-healthcare communications services to a common delivery point. With tens of millions of patients being admitted to U.S. hospitals on an in-patient basis every year, the number of "bored hackers" given access to such a system could be quite high, assuming even a modest proliferation of the combined delivery architecture. The impact of a successful penetration of a healthcare resources by a malcontent patient, with or without the aid of the Internet, may potentially put hospital efficiency and patient lives at risk, as well as expose the hospital to the risk of major lawsuits and/or public embarrassment.

Thus, there remains a need in the healthcare industry for preventing an attack on healthcare data processing resources in a hospital information system, thereby thwarting malicious attempts at hacking into medical records and other sensitive information stored in the hospital information system.

SUMMARY OF THE INVENTION

In accordance with a first broad aspect, the present invention seeks to provide a system, comprising healthcare data processing resources; non-healthcare data processing resources; a switching entity disposed between the healthcare data processing resources and the non-healthcare data processing resources; and a communication link connected to the switching entity and connectable to an end user device. The switching entity is operative to alternatively support, over the communication link, either a healthcare session between the end user device and the healthcare data processing resources, or a non-healthcare session between the end user device and the non-healthcare data processing resources. The switching entity is configured to prevent the healthcare data processing resources and the non-healthcare data processing resources from communicating with each other via the switching entity.

In accordance with a second broad aspect, the present invention seeks to provide an access controller, disposed between healthcare data processing resources and non-healthcare data processing resources, and connectable to an end user device via a communication link. The access controller comprises a switching entity capable of operation in a first state in which the end user device is communicatively coupled to the healthcare data processing resources to support a healthcare session and a second state in which the end user device is communicatively coupled to the non-healthcare data processing resources to support a non-healthcare session; and a control entity for controlling the state in which the switching entity operates.

In accordance with a third broad aspect, the present invention seeks to provide a method, comprising: receiving an authentication request message from a user along a communication link; determining, from the authentication request message, whether the user is claiming to be a healthcare user or a non-healthcare user; sending the authentication request message to a selected one of a healthcare authentication entity and a non-healthcare authentication entity in dependence upon the determining; responsive to successful authentication by the selected authentication entity, controlling the state in which a switching entity operates, wherein the switching entity is capable of operation in a first state in which the end user device is communicatively coupled to healthcare data processing resources to support a healthcare session and a second state in which the end user device is communicatively coupled to non-healthcare data processing resources to support a non-healthcare session.

In accordance with a fourth broad aspect, the present invention seeks to provide a computer-readable storage medium containing a program element for execution by a computing device to implement the aforementioned access controller.

In accordance with a fifth broad aspect, the present invention seeks to provide an end user device, comprising: a processing unit operative to support, during non-overlapping time periods, distinct communications sessions with corresponding data processing resources in a network, the communications session supported during each of the time periods being one of a healthcare session and a non-healthcare session; and a memory for storing data exchanged between the processing unit and the network during the communications sessions. The memory is responsive to termination of communications sessions that are non-healthcare sessions to purge data stored into the memory during said sessions.

In accordance with a sixth broad aspect, the present invention seeks to provide a computer-readable storage medium containing a program element for execution by a computing device to implement the aforementioned end user device.

These and other aspects and features of the present invention will now become apparent to those of ordinary skill in the art upon review of the following description of specific embodiments of the invention in conjunction with the accompanying drawings.

DETAILED DESCRIPTION OF THE EMBODIMENTS

Overall Architecture

Figure 1:
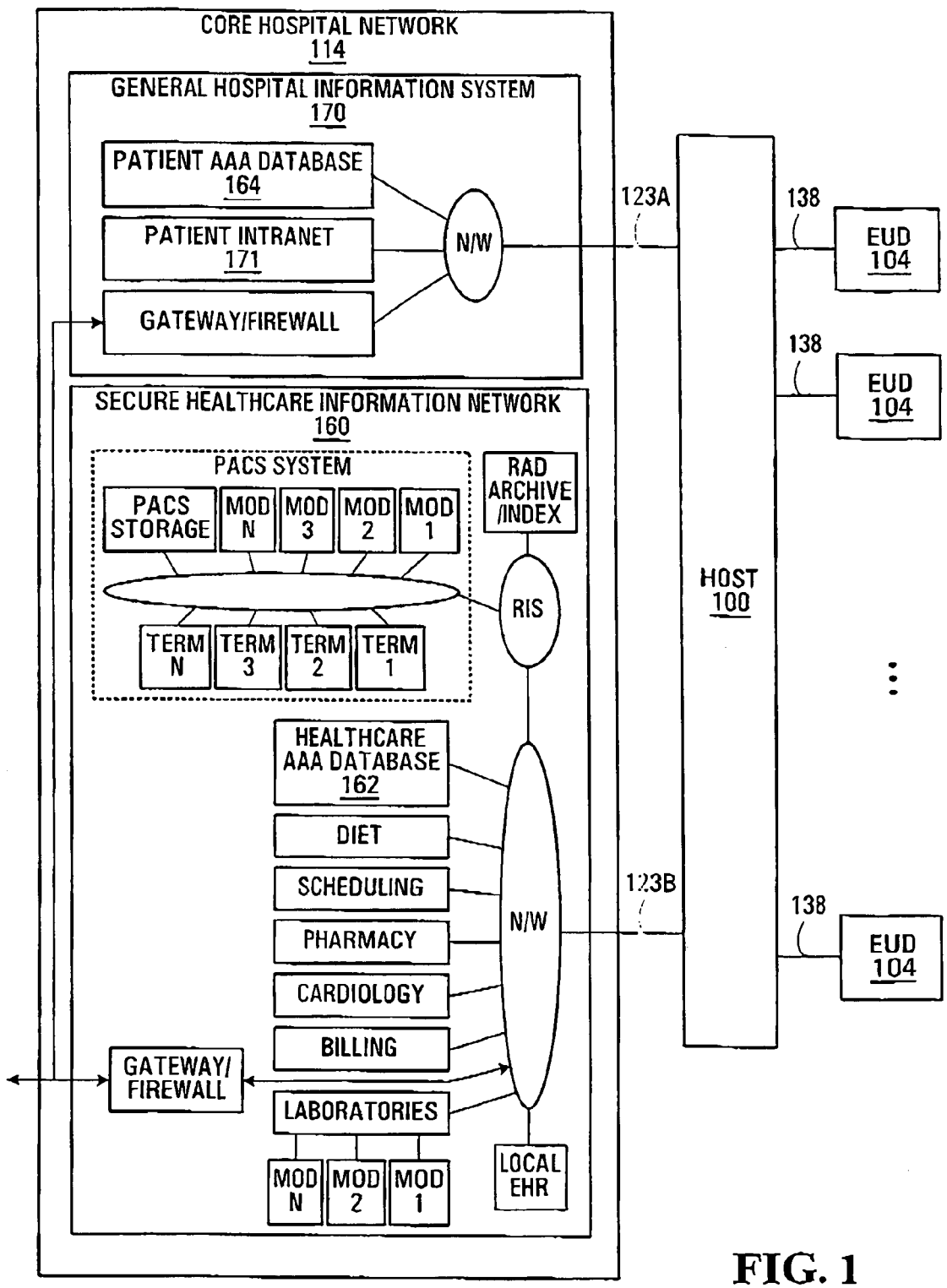
FIG. 1 shows a detailed block diagram of a core hospital network.
Figure 2:
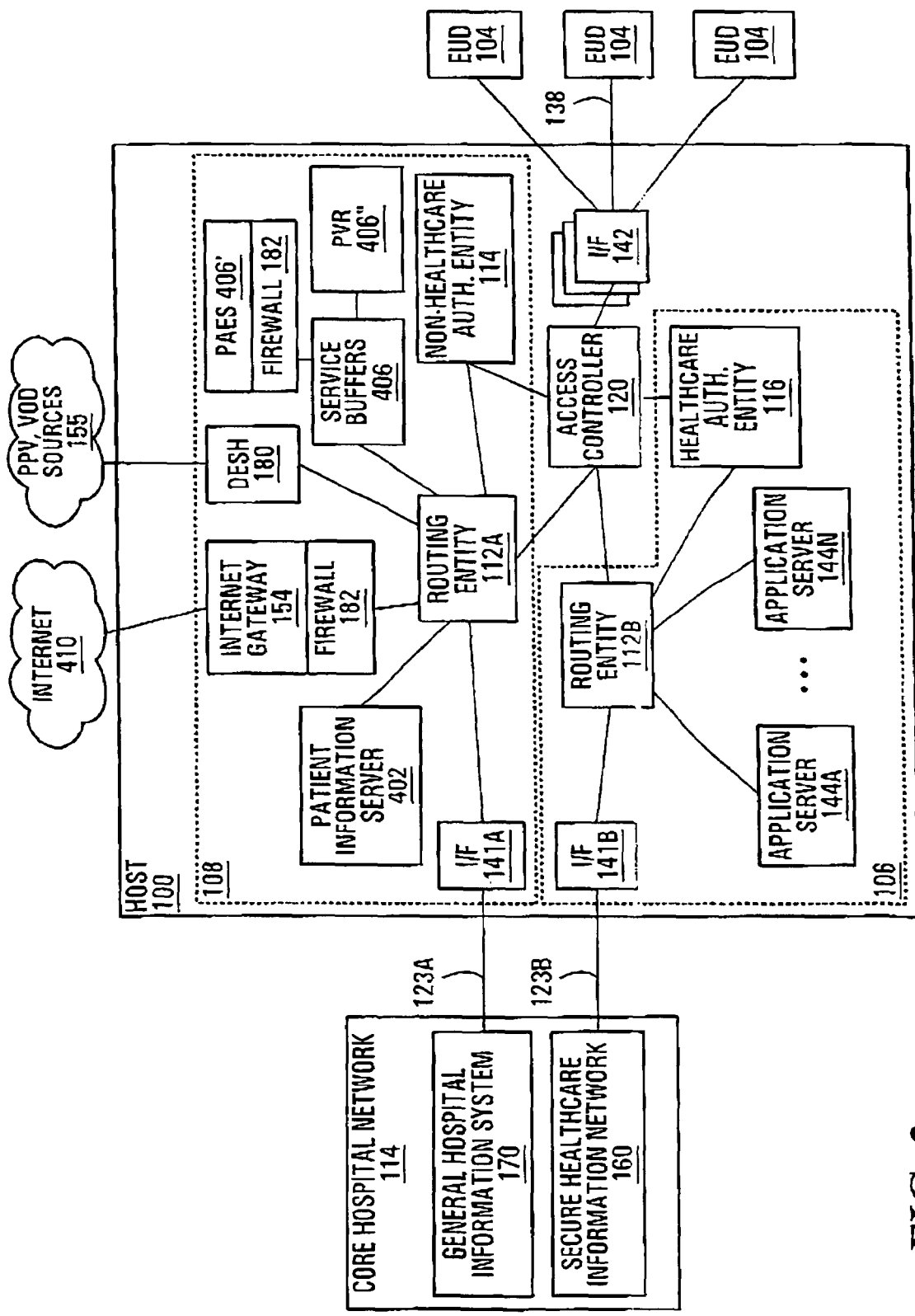
FIG. 2 shows a detailed block diagram of a host processing entity.
Figure 3:
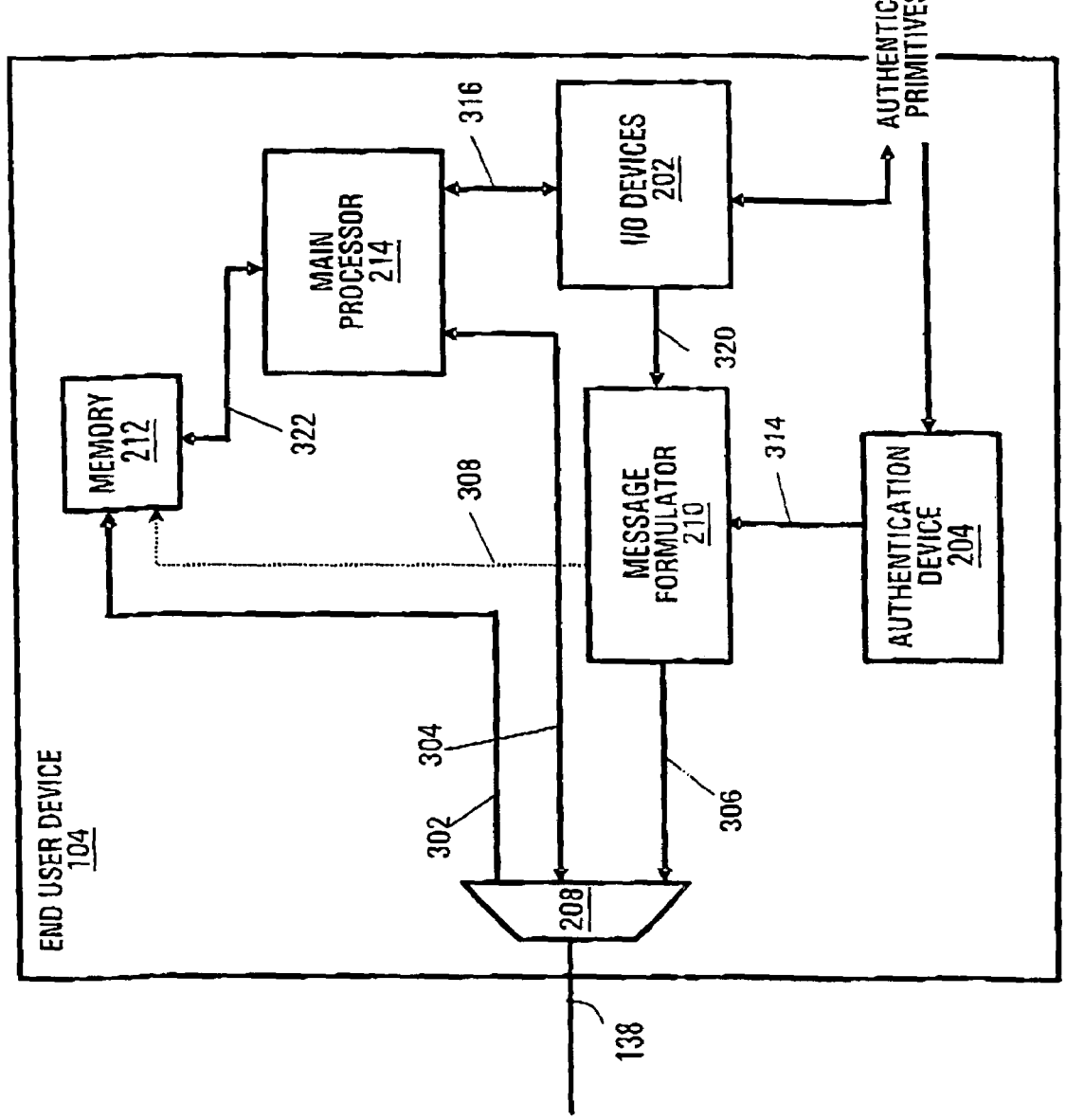
FIG. 3 shows a detailed block diagram of an end user device.

With general reference to FIGS. 1-3, there is shown an architecture for delivering healthcare communications services (e.g., CPOE) to the point of care (POC) for healthcare users, while also delivering non-healthcare communications services (e.g., information, communications and entertainment) to non-healthcare users at their respective locations. This is hereinafter referred to as an integrated healthcare/non-healthcare data delivery architecture. The integrated healthcare/non-healthcare data delivery architecture comprises a host processing entity 100 (hereinafter "host") and which consists of one or multiple instantiations, based on size, capacity, physical partitioning, and other factors, disposed between a core hospital network 114 and a plurality of end user devices 104. One instantiation of host 100 is shown in FIG. 2 but it is understood that other partitionings and instantiations are equally possible.

Generally speaking, the basic functionality of the healthcare data delivery aspect of this integrated architecture is to provide authenticated healthcare users with real-time bidirectional access to a suite of clinical tools and databases which can assist their productivity and accuracy while interacting with the patient and making decisions about the patient's condition and treatment. It does this by providing access to a suite of clinical services and applications that may reside in the end user device 104, in the host 100 or in both locations, in order to access records of the patient, including historical records, results from recent/ongoing tests, previous/ongoing treatments and drug regimens, etc., while also allowing the healthcare user to capture his/her decision on patient condition, diagnosis, treatment orders and drug orders to the pharmacy, etc., in a direct entry process proven to reduce the incidence of clinical errors. Such a real-time approach allows the use of real-time Decision Information Support Tools (DIST) which can reside in the core hospital network 114 or which might reside as a service on a server in the host 100. Such tools provide validation of clinician orders, for instance by checking medical records for other drug prescriptions that are in effect which might lead to a drug interaction with the newly prescribed drug and cause an adverse drug reaction (ADR). The system achieves this required functionality by first properly authenticating the healthcare user to be who he/she claims to be, then admitting them on a limited basis to the host 100 and the core hospital network 114, based upon their access profile. The healthcare user can then access the necessary clinical tools residing on the end user device 104 or the host 100 to access healthcare data for those patients they are authorized to access to a level of read, read/write or write access as allocated from an AAA server located in the core hospital network 114.

On the other hand, the basic functionality of the non-healthcare data delivery aspect of this integrated architecture is to support a wide range of entertainment and information services for non-healthcare users. Examples of services that may need to be provided to the non-healthcare user, under various levels of authentication, include but are not limited to television, access to pay per view (PPV) and video on demand (VOD) movies, Internet access, intranet access for various hospital functions (such as patient education, dietary, etc.), electronic mail, and so on. These services are delivered using a common delivery infrastructure, specifically, one which is shared with the infrastructure used to deliver the healthcare services described above. The use of an integrated architecture can thus provide significant capital, installation and operating cost savings.

The end user device 104 is located at a common delivery point at the point of care (POC). An example of a point of care is a patient bedside or a ward. Another example of a point of care is an operating theater or an examination room. In the case where the end user device 104 is a wireless mobile device carried by a healthcare user, the POC will be governed by movement of the healthcare user, although in this case there may be less of a need to deliver non-healthcare communications services than in the case where non-healthcare users have access to the same terminals as healthcare users, which is generally, but not necessarily exclusively, in the bed wards of hospitals.

The host 100 communicates with each end user device 104 via a respective communications link 138, which may be either an entirely fixed-wire link or a partly fixed-wire and partly wireless link or even a completely wireless link, depending on the nature of the end user device 104 and the intermediate access transmission system. The communications link 138 may be implemented as a physical end-to-end link or it may be in series with a virtual encrypted link over an interposed general purpose network. Suitable non-limiting examples of fixed-wire cabling for the communications link 138 include coaxial cable, as well as twisted pair (e.g., access-side PBX, Cat 2-3 or Cat 5). In another embodiment, the host 100 is connected via Ethernet connections (e.g., native Ethernet or Ethernet over DSL) to wireless base stations or access points to provide wireless LAN service to areas (such as examination rooms) throughout the hospital.

In order to provide communication between the host processing entity 100 and the end user devices 104 in accordance with the integrated architecture of an embodiment of the invention, a common access infrastructure is used to provide both the healthcare communications services and the non-healthcare communications services. In an embodiment, the common cabling may use part of a pre-existing cabling infrastructure (e.g., point-to-point telephone cabling) for the purposes of implementing the links 138 to various end user devices 104. This is to avoid having to install a new wiring base, which could have disruptive impacts on the areas surrounding the installation, in that patients have to be removed from rooms where walls or ceiling or other "unclean" spaces are being opened. For more information regarding the use of a common access infrastructure for integrated delivery of both healthcare communications services and non-healthcare communications services, the reader is referred to the U.S. patent application Ser. No. 10/813,230 entitled "Integrated And Secure Architecture For Delivery Of Communications Services In A Hospital" to Graves et al., filed Mar. 31, 2004, incorporated by reference herein.

In addition to providing delivery of healthcare and non-healthcare communication services over a common access infrastructure, the architecture of the present invention may also simultaneously deliver basic analog or digital telephony. In this case, head end equipment provided at the host 100 would provide hybridizing functionality, and corresponding outstations would be installed remotely from the head end equipment, at some point further along the telephony plant. In this way, outstations are connected to telephone devices as well as to end user devices 104. For more information regarding the use of telephony cabling for delivery of telephony along with non-telephony communications services, the reader is referred to the above-mentioned U.S. provisional patent applications (Ser. No. 60/503,965 and Ser. No. 60/505,941), both incorporated by reference herein.

Core Hospital Network 114

With continued reference to FIG. 1, the core hospital network comprises a general hospital information system (GHIS) 170 and a secure healthcare information network (SHIN) 160, which are connected to the host 100 via communication links 123A and 123B, respectively. The secure healthcare information network 160 interconnects various hospital entities, such as radiology (connected to a PACS system), diet, scheduling, pharmacy, cardiology, billing, laboratories, local electronic health records, etc. The secure healthcare information network 160 also maintains a healthcare AAA database 162, which contains information allowing healthcare users to be authenticated. In an embodiment, the healthcare AAA database 162 comprises a collection of healthcare user identities and securely held corroborating evidence, along with an associated access profile for each healthcare user, which will include a dynamic patient access list based on the hospital's admissions database together with a specific mapping of who has what accessible data, based upon professional qualifications, status and allocation to patient treatment teams, which itself may be dynamic, especially for shift workers such as nurses. The secure healthcare information network 160 further interconnects to the general hospital information system 170 via a firewall. For its part, the general hospital information system 170 allows access to a patient intranet 171 and maintains a non-healthcare AAA database 164. In an embodiment, the non-healthcare AAA database 164 comprises a collection of non-healthcare user identities and securely held corroborating evidence, along with an associated access profile for each non-healthcare user. The healthcare AAA database 162 receives its patient admissions input from a hospital admissions server (not shown), and the non-healthcare AAA database 164 may or may not be partially or wholly managed by that same hospital admissions server or another server altogether.

End User Device 104

For the purposes of this description, and by way of example only, the end user device 104 could be a fixed-wire device or a mobile wireless device. With reference to FIG. 3, the end user device 104 comprises a network interface 208, a main processor 214, a message formulator 210, a set of I/O devices (including data entry and data display devices) 202, one or more authentication device(s) 204, a memory store (e.g., RAM and/or hard drive) 212. Other elements, such as a session data control module, are not shown here but are described in greater detail in the U.S. patent application Ser. No. 10/813,358 entitled "Systems And Methods For Preserving Confidentiality Of Healthcare Information In A Point-Of-Care Communications Environment" to Graves et al., filed Mar. 31, 2004, incorporated by reference herein.

The message formulator 210 is responsible for formulating authentication request messages based on authentication primitives 900 received from the authentication device 204 (via link 314) and possibly the I/O devices 202 (via link 320). Specifically, the message formulator 210 first performs a high-level validation to determine whether the authentication primitives 900 comply with an expected data format for a particular "user class", without actually performing authentication of the user. The two main examples of "user class" as used herein include a healthcare user class, and a non-healthcare user class (which can include bona fide admitted patients and their registered or unregistered visitors). However, it should be understood that the healthcare user class may further be broken down into sub-classes such as clinicians (physicians, nurses, technicians) and non-clinicians (orderlies, contractors). In fact, the definition of classes is dictated only by operational requirements and thus may lead to different definitions for different practical applications.

Upon successful high-level validation, the authentication request message formulator 210 creates an authentication request message, which will contain the entered authentication primitives 900 and additional data (e.g., in the form of a marker, address or formatting difference) which encodes the user class, allowing the access controller 120 in the host 100 to correctly onwardly route the authentication request message to one of the authentication entities 116, 114. It is noted that the formulation of authentication request message is isolated from the main processor 214 and so cannot be tampered with by software downloaded into that processor.

The message formulator 210 is operable to send the generated authentication request messages to network interface 208 via a link 306. Optionally, the message formulator 210 is also operable to detect when the user has requested to terminate or suspend the current "session", either explicitly by an end-of-session command or series of commands interpreted from the keyboard inputs or from the withdrawal of an enabling element, such as an authentication device 204, or implicitly by specifying a new set of authentication primitives. Such a message indicative of session termination or suspension is sent via an optional memory purge line 308 to memory store 212 causing a memory purge of the data loaded during the terminated session.

In a non-limiting embodiment, the end user device 104 can be a PC-based workstation, where the memory store 212 is a combination of hard drive and volatile memory (e.g., RAM). The hard drive can be used to store an operating system, I/O drivers and software for start-up, human-machine interface (HMI), display formatting and data collection, as well as healthcare application software. In such an embodiment, there may be some security risks due to storage of healthcare information on the hard drive, which of course retains storage when the unit is de-powered, and allows that healthcare information to be revealed if stolen or probed. This security risk can be reduced by appealing to techniques for preserving the confidentiality of healthcare information stored in end user device. For examples of such techniques, the reader is referred to the U.S. patent application Ser. No. 10/813,358 entitled "Systems And Methods For Preserving Confidentiality Of Healthcare Information In A Point-Of-Care Communications Environment" to Graves et al., filed on Mar. 31, 2004 and incorporated by reference herein in its entirety.

In another non-limiting embodiment, the end user device 104 is a "thin client", whereby the end user device 104 is dependent upon the network servers (in this case application servers 144A-N for healthcare users, and Internet gateway 154, digital entertainment services head end 180 and service buffers 406, etc. for non-healthcare users). In this case, much of the operating complexity of the end user device 104, as well as the memory requirements of the end user device 104 (especially due to complex operating systems and software applications) can be reduced. This results in the memory store 212 becoming a volatile memory containing a simple, downloaded, "thin client" operating system and data. Alternatively, the memory store 212 may be a combination of volatile memory for downloaded data and a non-volatile read-only-memory for the operating system. Note that in such an embodiment, the non-volatile store is read-only and, unlike a hard drive, cannot be written to. The memory store 212 stores data required for the main processor 214 to run a dependent "thin client" session with one of the application servers 144A, . . . , 144N, for a particular user of the end user device 104. This data may include a downloaded operating system, I/O drivers and software for human-machine interface (HMI), display formatting and data collection. In addition, the data to be stored in the memory store 212 may be delivered in pages formatted in the host 100 for display via one of the I/O devices 202, analogous to web pages. The portions of the data corresponding to sensitive healthcare information may be stored in a predetermined portion of the memory store 212. The data being written to and read from the memory store 212 by the main processor 214 is carried along a link 322.

The memory store 212 is connected by a memory purge line 302 to the network interface 208 and by the previously described memory purge line 308 to the message formulator 210. Each memory purge line 302, 308 has the potential to carry a signal which purges the memory store 212 of data loaded during the course of the most recent session, especially when this session is a non-healthcare session. Purging can be achieved in a variety of ways, including but not limited to erasing, deleting, over-writing, scrambling and/or resetting a section of the memory store 212, possibly even the entire memory store 212. The use of purged volatile read-write memory and of non-volatile ROM ensures that the end user device 212 cannot be used as a storage device for spyware, etc. downloaded via the non-healthcare data processing resources 108 and subsequently used to attack the healthcare data processing resources.

The main processor 214 manages the processing load presented by the operating system, and runs local applications which are primarily associated with data collection, formatting and display. For example, the main processor 214 may implement a web browser for receiving user input from the I/O devices 202 via link 316, displaying still images and interacting with the user via input boxes for applications which have been centralized in the host 100. Despite the "thin client" nature of the end user device 104, there may be sufficient resources to implement an MPEG decoder or media player for display of video images, and a voice codec for audio input/output. The main processor 214 accesses the memory store 212 via link 322.

The authentication device 204 may include one or more of, for example, a magnetic card reader, a bar code scanner (e.g., for reading a user's bracelet), a biometric (e.g., fingerprint, iris) scanner, etc., the operation of which may or may not be augmented by a password or PIN. The authentication device 204 receives authentication primitives input by the user. The authentication device 204 supplies these authentication primitives to the message formulator 210 via a link 314.

The I/O devices 202 may include, for example, a keyboard/mouse arrangement with a display having a built-in touch screen. The I/O devices 202 receive input (e.g., physician order entries and responses, etc.) which is provided to the main processor 214 via a link 316 for transmission to the host 100 via the network interface 208. The I/O devices 202 also receive data from the main processor 214 via the link 316 which is to be output to the user (e.g., in the form of an image or sound). The I/O devices 202 may also receive some of the authentication primitives (e.g., user name and password or PIN) input by the user. If this is the case, the I/O devices 202 provide these authentication primitives to the message formulator 210 via a link 320.

The network interface 208 is connected to the main processor 214 via a link 304, to the memory via a memory purge line 302 and to the message formulator 210 via a link 306. The network interface 208 may comprise a multiplexer. In a downstream direction (host 100 to end user device 104), the network interface 208 recognizes messages destined for the main processor 214 as well as messages requiring a purge of the memory store 212. The network interface 208 has the capability to discern the various types of messages and route them to the proper functional element via memory purge line 302 or link 304, as appropriate. In the upstream direction (end user device 104 to host 100), the network interface 208 receives messages destined for the host 100 as received from the message formulator 210 via link 306 and from the main processor 214 via link 304. The network interface 208 has the capability to combine these messages and transmit them to the host 100 along the communications link 138.

By virtue of its multiplexing operation, which multiplexes outbound traffic separately from demultiplexing incoming traffic with no possibility of an outbound-to-inbound loop-around, the network interface 208 prevents outgoing messages from the main processor 214 on link 304 or authentication request messages from the message formulator 210 on link 306 from reaching the memory store 212 via the memory purge line 302. This isolation of communication channels provides added security, should the main processor 214 become contaminated with illicit downloaded software. Also, by virtue of its multiplexing functionality, the network interface 208 prevents authentication request messages from the message formulator 210 on link 306 from reaching the main processor 214 via link 304. This isolation of communication channels provides added security, preventing the main processor 214 and its own memory from reading and storing user-initiated authentication request messages.

Host 100

With reference to FIG. 2, there is shown a first variant of the host 100, in which healthcare and non-healthcare communications services are generated independently and merged at the point of delivery over a common delivery infrastructure throughout the hospital. This first variant of the host 100 comprises an interface (I/F) 142, an access controller 120, healthcare data processing resources 106 and non-healthcare data processing resources 108. The healthcare data processing resources 106 comprise a routing entity (router) 112B to which are connected a healthcare authentication entity 116, a plurality of application servers 144A, . . . , 144N and an interface (I/F) 141B. The interface 141B connects to the secure healthcare information network 160 via link 123B. The access controller 120 has direct links to the routing entity 112B as well as to the healthcare authentication entity 116.

The application servers 144A, . . . , 144N are responsible for running and executing healthcare applications (such as a CPOE service, decision information support tools, prescription drug order entry service, radiology image viewing service, etc.) and storing temporary medical data (volatile or otherwise) as well as acting as host processors or servers for the dependent thin client end user devices 104. One or more of the application servers 144A, . . . , 144N may also be responsible for data gathering from the core hospital network 114, which is achieved by communicating with a department in the secure healthcare information network 170 via the routing entity 112B and the interface 141B. This may require access to the secure healthcare information network 160 and therefore the particular healthcare application may comprise a data mining sub-function which places data requests to the secure healthcare information network 160 and receives the requested data in return. The healthcare application servers 144A, . . . , 144N are operative to open a healthcare "session" once the user has been successfully authenticated, at which point the healthcare application servers 144A, . . . , 144N begin configuring data for the end user device 104, including display characteristics, screen presentation, graphics, active information, input boxes, etc. For example, a page formatter can provide data for the end user device 104 in pages that are pre-formatted for display.

In a small hospital the application servers 144A, . . . , 144N might be implemented on a single computing device, whilst in a larger hospital deployment, with perhaps hundreds of terminals, a single computer-based server would be inadequate. Hence, the application servers 144A, . . . , 144N evolve into an application server complex with various specialized servers interconnected by a router or switch and with one server providing the master sequencing and data display formatting. The use of a server complex has several advantages. Firstly, multiple application servers can provide some form of protection against failure so that, in the event of a server failure, the system slows down but does not fail, with other servers picking up the traffic load of the failed server. Also, a centralized suite of servers makes application software upgrades much smoother and easier, especially relative to trying to upgrade such software if it were resident in mobile devices, some of which are guaranteed not to be on-site at the time of upgrade, in addition to the sheer number of machines to upgrade. Additionally, an individual server can be taken out of service for an upgrade or for application suite upgrade without taking the system down, and that upgrade can be exhaustively checked before returning the server to the system.

The non-healthcare data processing resources 108 comprise a routing entity (router) 112A to which are connected a non-healthcare authentication entity (PA) 114, service buffers 406 which contain (i) video services buffering functionality (including, e.g., personal video recorders (PVRs 406") for allowing non-healthcare users to record movies and play them back at a later time, in the event the non-healthcare session needs to be interrupted) as well as (ii) processing service buffers (i.e., the Patient Application Execution Server (PAES) 406') where computer applications such as Internet downloads, games, etc. are run in a secure firewalled environment, a digital entertainment service head end (DESH) 180, a patient information server (PIS) 402, which provides access to a patient-accessible information suite—for instance hospital services, billing, dietary selections, etc., an Internet gateway (IGW) 154 and an interface (I/F) 141A. The interface 141A connects to the general hospital information system 170 via link 123A. The access controller 120 has direct links to the routing entity 112A as well as to the non-healthcare authentication entity 114.

Various services can be delivered as packetized switched digital signals from the digital entertainment services head end 180. For example, the digital entertainment services head end 180 generates digitized streaming video feeds from input analog CATV channels by a process of digitization or directly receives digitized CATV feeds from the service provider. The digital entertainment services head end 180 may also provide streaming video feeds for pay-per-view (PPV) channels or video-on-demand (VOD) channels, either generated locally or provided from a PPV or VOD source 155 (e.g., a service provider in-feed). Each non-healthcare user is in effect a subscriber into this system, having been granted a priori, pre-purchased, or spot-purchased a specific authentication and authorization level, and the non-healthcare authentication entity 114, upon receiving a request from the non-healthcare user, validates that request and then authorizes the release of the requested program material from the digital entertainment services head end 180. The digital entertainment services head end 180 then delivers a flow of streaming video as a stream of IP-based packets, through to the end user device 104, where they are converted, via a media player or an MPEG decoder, into sound and video for presentation to the non-healthcare user.

In the event that the non-healthcare user needs to interrupt a PPV or VOD stream (or even optionally the basic TV feed) for whatever reason, then that stream can be diverted via a switching action into the digital video portion of the service buffer 406, which is basically a large multi-functional store. In this case, the service buffer 406 implements the function of a digital personal video recorder (PVR) 406" which would store the video, up to a certain maximum amount, until the non-healthcare user is ready to resume viewing the material, in which case the PVR 406" would remain in series with the digital entertainment services head end-patient feed to act as a "time shifter" until the end of that particular program, PPV session or VOD session, as well as storing an "image" of a non-healthcare session when interrupted by a transfer to a healthcare session. The storing of such image is useful to allow the patient to resume where his/her non-healthcare session left off, once the memory store 212 is purged at the end of the non-healthcare session. Then direct connectivity would be resumed between the digital entertainment services head end 180 and the non-healthcare user. This feature allows a clinician to interrupt a non-healthcare user's viewing experience (e.g., to carry out a series of clinical activities), without costing the non-healthcare user the loss of material that the non-healthcare user has purchased and without causing patient anguish. For more details regarding the handling of an interruption of a non-healthcare session, the reader is referred to the U.S. patent application Ser. No. 10/813,230 entitled "Integrated And Secure Architecture For Delivery Of Communications Services In A Hospital" to Graves et al., filed Mar. 31, 2004, incorporated by reference herein.

In addition, under control of the non-healthcare authentication entity 114, the non-healthcare user can gain a profiled access to the patient information server 402, which is basically a processor running various applications to permit data access to the general hospital information system 170 (for information/services such as dietary planning) and can gain access to the Internet gateway 154 that will permit the non-healthcare user to browse the web, prepare and send/receive e-mail, etc., on a machine located in the host 100. For added security, non-healthcare users might can be restricted to downloading and/or running applications from the Internet in a secure part of the host 100 (e.g., in the service buffer 406 or the patient information server 402 or another separate firewalled, protected server function, termed the "Patient Application Execution Server" (PAES) 406'), which would have a strong series of defenses against "unfriendly" software (viruses, worms, spyware of various types, denial-of-service software, etc.) downloaded deliberately or accidentally from the Internet.

As a result the non-healthcare user can have TV, VOD and PPV entertainment, browse the internet, compose or receive e-mails and/or make use of the hospital intranet services via the patient information server 402 in a common integrated, but securely partitioned, infrastructure. Furthermore a secure path can be provided to a VoIP portal off of the hospital PBX or via an Internet-based telephony offering, or by other means permitting telephony service to the non-healthcare user at the bedside. Alternatively, the pre-existing phone system can be retained.

It is noted that since the healthcare data processing resources 106 and/or the non-healthcare data processing resources 108 (or indeed the entire host 100) do not need to be at the point of care, they may be advantageously be kept in a secure location such as a HIS Information Technology Center or even a PBX room, since this provides the epicenter for the telephony wiring. Advantageously, this allows the entire host to be located at a central location which is at the confluence of all the incoming wiring from the terminals throughout the hospital (or at a location easily connected to the confluence of the wiring.)

In a second variant of the host 100, a common routing entity achieves the dual functionality of routing entities 112A, 112B by using two sets of ports, each used for a separate routing function. Thus, the routing entity, which can be a routing complex, would be connected to the healthcare authentication entity 116, the plurality of application servers 144A, . . . , 144N, the interface (I/F) 141B, the non-healthcare authentication entity 116, the service buffers 406, the digital entertainment service head end (DESH) 180, the patient information server 402, the Internet gateway 154 and the interface (I/F) 141A. Here, the access controller 120 would have direct links to the routing entity 112 in addition to the direct links to the healthcare authentication entity 116 and the non-healthcare authentication entity 114.

Of course, there may be more than just two classes of users requiring mutually exclusive access, in which case additional authentication entities beyond the healthcare authentication entity 116 and the non-healthcare authentication entity 114 can be provided. Generally speaking, the use of separate authentication entities for the purposes of authenticating users belonging to separate user classes has the advantage of preventing scenarios where, by accident or malice, a patient would be authenticated as a clinician, or an orderly would be authenticated as a patient, etc. Such separation prevents AAA messages intended for one AAA server and from that server's clientele from reaching any other AAA server, where it may be misinterpreted as a legitimate message within its service class, resulting in a breach of security. Specifically, this separation is achieved due to operation of the access controller 120, as described in greater detail in the U.S. patent application Ser. No. 10/813,230 entitled "Integrated And Secure Architecture For Delivery Of Communications Services In A Hospital" to Graves et al., filed Mar. 31, 2004, incorporated by reference herein.

In a wireless scenario, the connectivity between individual ports at the interface 142 and the end user devices 104 accessing those ports is no longer static, with both mobility (different terminals attaching to the same port) and roaming (terminals moving between ports) being possible. Thus, in the wireless scenario, there is provided a network of wireless LAN access points that is connected to the interface 142 over a fixed-wire link and that communicates over a wireless link to one or more end user devices 104. Since the wireless LAN access point can simultaneously service multiple remote terminals, this requires that multiple concurrent but entirely separate sessions to multiple end user devices 104 (operating under different users and authentications) be accommodated on a single port into the interface 142. The leads to the requirement that multiple concurrent and/or overlapping sessions, each with a potentially unique user access policy, be supported on a common port. It is the role of a wireless security switch (WSS) (an available entity associated with the control of WLAN users and security), to meet these requirements by handling the multiple connections to various end user devices, as well as authentication at a device level. In addition, the wireless security switch handles to wide variety of security threats and attacks not encountered in fixed-wire solutions.

Access Controller 120

One role of the access controller 120 is to cooperate in providing an environment that insulates the healthcare data processing resources 106 against the small percentage of "bored hackers" who will have a prolonged time on their hands in a hospital setting and access to the Internet via the non-healthcare resources 108. Specifically, while the Internet gateway 154 and the PAES 406' should be engineered with good state-of-the-art firewall technology 182 between these resources and the rest of the system (via the routing entity 112A), in the passage of time such software-based defenses are liable to be circumvented (as has recently been illustrated by the simple disguising of malicious software to emulate normal password-protected ZIP files). Hence, in line with the best practices of "layered security", the access controller 120 is designed in order to provide an additional layer of security to prevent the healthcare data processing resources 106 from being compromised by either a denial-of-service attack spawned directly from the Internet or spyware downloaded during a non-healthcare session. Such spyware may to attempt capture key data, potentially up to and including authentication request messages content, depending upon the end user device 104 architecture and the visibility of such messages to the main processor 214. Of course, by isolating the separate main processor 214 from the message formulator 210, this provides an added layer of security. Yet another layer is provided by using a thin client architecture which purges spyware (and other data) loaded during a non-healthcare session at the end of that session. Thus, one of the roles of the access controller 120 is to control when and how the end user device 104 is connected to which resources in the host 100, and when and how the internal memory of the end user device 104 is purged to ensure that a) the end user device 104 is connected to the appropriate data processing resources (106 or 108); b) only legitimate authentication request messages are processed and and acted upon only after proper authentication by the appropriate AAA server 162, 164; and c) no residual spyware or other contaminant software can remain from a non-healthcare session and contaminate a healthcare session. These points are addressed in the following description of the access controller 120. Also, it is desirable that no sensitive healthcare (i.e., clinical) information remains stored in the memory store 212 of the end user device 104 after termination of a healthcare session or upon losing the connection to the host 100. This particular circumstance is dealt with as described in the U.S. patent application Ser. No. 10/813,358 entitled "Systems And Methods For Preserving Confidentiality Of Healthcare Information In A Point-Of-Care Communications Environment" to Graves et al., filed Mar. 31, 2004, incorporated by reference herein.

The access controller 120 communicates with the end user device 104 (via interface 142), as well as with the healthcare authentication entity 116, the non-healthcare authentication entity 114 and the routing entities 112A, 112B (or a single routing entity, as appropriate). The access controller 120 may be implemented by functional elements as now described with reference to FIG. 4. Of course, these functional elements can be implemented in hardware, software, firmware or a combination of the above. In the case of a software functional element, code defining the operation of that functional element can be downloaded to its various elements from a secure central site within the host 100 or core hospital network 114 to allow download of access control parameters such as the recognition of the formats used by the message formulator 210 (in the end user device 104) to generate authentication request messages for different user classes.

Figure 4:
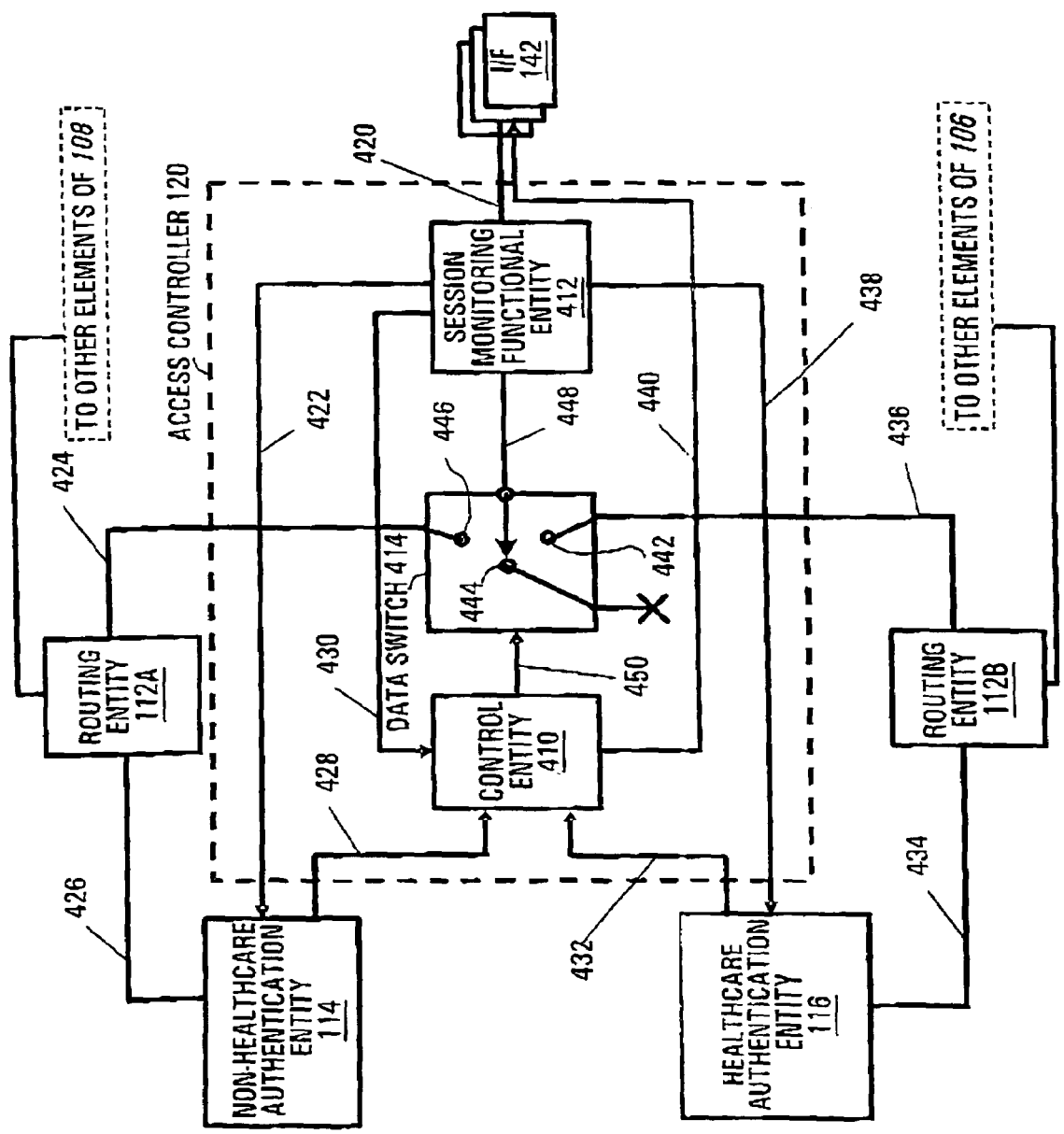
FIG. 4 shows a detailed block diagram of an access controller in the host processing entity of FIG. 2.

In the specific non-limiting embodiment of FIG. 4, the access controller 120 comprises a control entity 410, a data switch 414 and a session monitoring functional entity 412. The data switch 414 is connected to the routing entity 112A by a link 424, to the routing entity 112B by a link 436 and to the session monitoring functional entity 412 by a link 448. Conceptually, the data switch 414 has three "poles" 446, 444, 442, corresponding to three possible states "A", "B" and "C", respectively. In state "A", the data switch 414 is connected to the non-healthcare data processing resources 108 via the routing entity 112A and the session monitoring functional entity 412, and in state "C", the end user device 104 is connected to the healthcare data processing resources 106 via the routing entity 112B and the session monitoring functional entity 412.

In addition, the data switch 414 is capable of occupying a state "B", in which there is no connection between the end user device 104 and either the healthcare data processing resources 106 or the non-healthcare data processing resources 108 via the data switch 414. Control of the operational state of the data switch 414 is provided by the control entity 410, which may be integrated with the data switch 414. The control entity 410 sends control information regarding the state of data switch 414 along a link 450. In addition, the control entity 440 is connected to the interface 142 via a link 440, allowing it to send memory purge commands to the end user device 104 under certain circumstances to be described later on in greater detail.

It should be understood that while the description is best understood from a hardware point of view, the data switch 414 need not be a hardware entity. Rather, it may occupy different states simultaneously, for different sessions running concurrently with a plurality of end user devices 104. For example, a first virtual connection may be established between a first end user device and the healthcare data processing resources 106 via the data switch 414, while a second virtual connection may be established between a second end user device and the non-healthcare data processing resources 108 via the data switch 414. In general, any hardware, software or firmware implementation for the data switch 414 is appropriate, as long as measures are taken to allow each end user device sharing a common memory store 212 to be involved in at most one session at a time (with either the healthcare data processing resources 106 or the non-healthcare data processing resources 108).

The session monitoring functional entity 412 is connected to the data switch via link 448, which allows it to be alternatively connected to either the routing entity 112A or the routing entity 112B. In addition, the session monitoring functional entity 412 is connected to the non-healthcare authentication entity 114 by a link 422 and to the healthcare authentication entity by a link 438. A link 420 connects the session monitoring functional entity 412 to the interface 142. As will be described in greater detail below, the session monitoring functional entity 412 controls the extraction, processing and routing of session messages arriving from the end user device 104 via the interface 142 and link 420 or arriving from the routing entity 112A or the routing entity 112B via link 424 or 436, respectively.

Figure 5A:
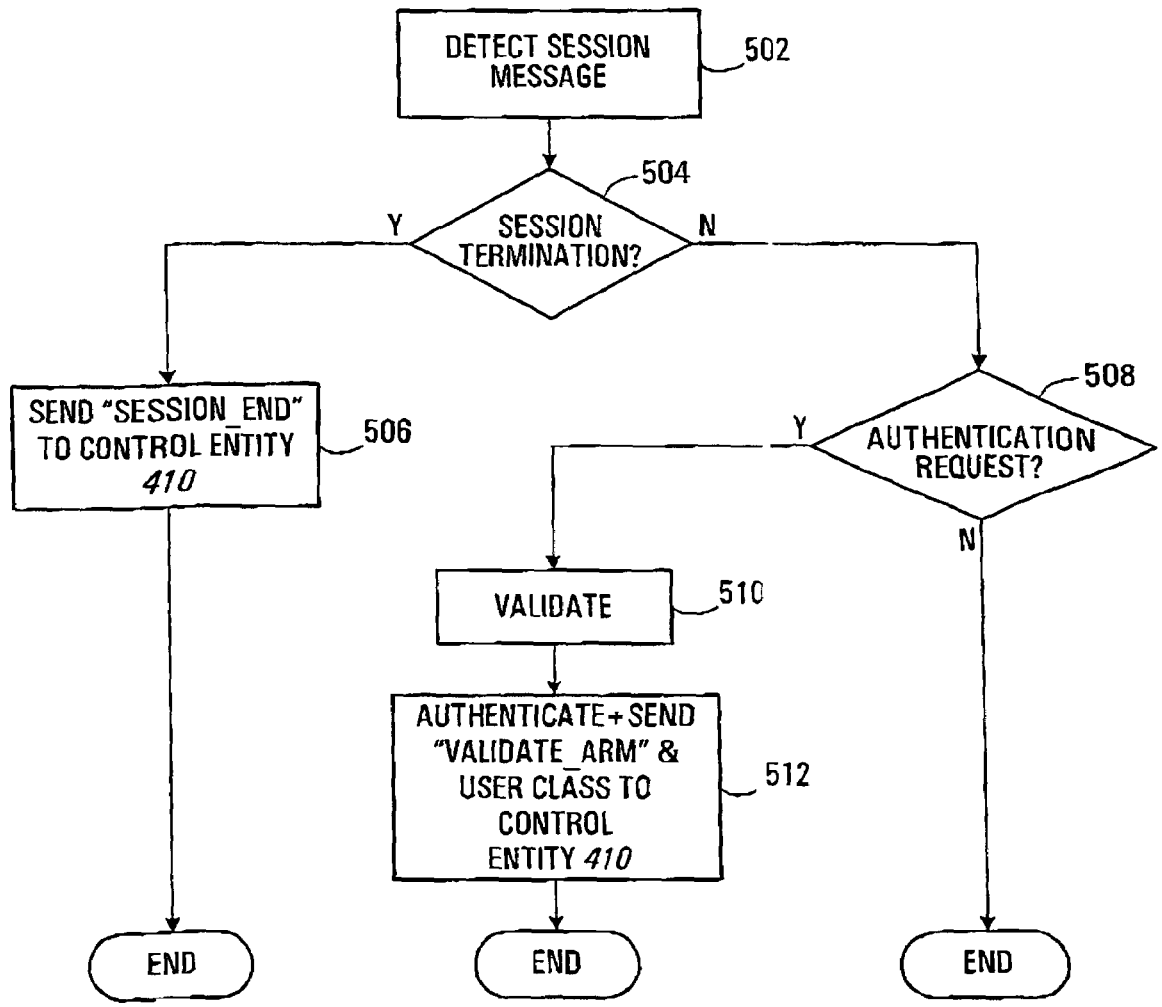
FIGS. 5A-5D are flowcharts illustrating operation of various elements of the access controller of FIG. 4.

Operation of the session monitoring functional entity is now described in conjunction with the flowchart of FIG. 5A. At step 502, the session monitoring functional entity 412 detects a so-called "session message", which can be, as checked at step 504, indicative of session termination. Such messages may be received from the end user device 104 or from deeper within the host 100. If indeed, such a message is received, then step 506 is executed, resulting in the transmission of a "SESSION_END" message to the control entity 410, which results in the control entity 410 setting the data switch 414 to port 444 and initiating a memory purge of the memory store 212 in the end user device 104, as well as optionally signaling the appropriate entity in the host 100 to take a "snapshot" of the session for archiving or context-saving purposes). If, however, the session message detected at step 502 is not indicative of session termination, it may be, as checked at step 508, an authentication request message. It is recalled that such messages are generated by the message formulator 210 in the end user device 104 in order to allow a new user to be authenticated. It will be appreciated that an authentication request message may be received during an ongoing session, i.e., during a time when the data switch is in state "A" or "C", as well as "B".

If indeed the received session message is an authentication request message, then step 510 is executed, where the authentication request message is "validated", i.e., processed on the basis of the fundamentals of how the message has been structured by the message formulator 210 in the end user device 104, in order to identify the user class associated with the authentication request message and thereby to select the authentication entity (in this case either 114 or 116) for which the authentication request message is destined. At step 512, the session monitoring functional entity authenticates the user by sending the authentication request message to the selected authentication entity via link 422 or 438, as appropriate. In addition, the session monitoring functional entity 412 sends a "VALID_ARM" (i.e., "valid authentication request message") to the control entity 410 as well as the user class (in this specific case, either healthcare user or non-healthcare user) associated with the authentication request message.

In order to determine in which state to put the data switch 414, the control entity 412 performs an algorithm, which relies on the current state of the data switch 414, as well as messages received from the non-healthcare authentication entity 114, the healthcare authentication entity 116 and the session monitoring functional entity 412. Examples of messages received from the healthcare authentication entity 116 and the non-healthcare authentication entity 114 include messages indicative of successful or unsuccessful authentication of a given user (the authentication process being initiated by the session monitoring functional entity 412 at step 512). As previously described, examples of messages received from the session monitoring functional entity 412 include the "SESSION_END" message sent at step 506 and the "VALID_ARM" message sent at step 512.

Figure 5B:
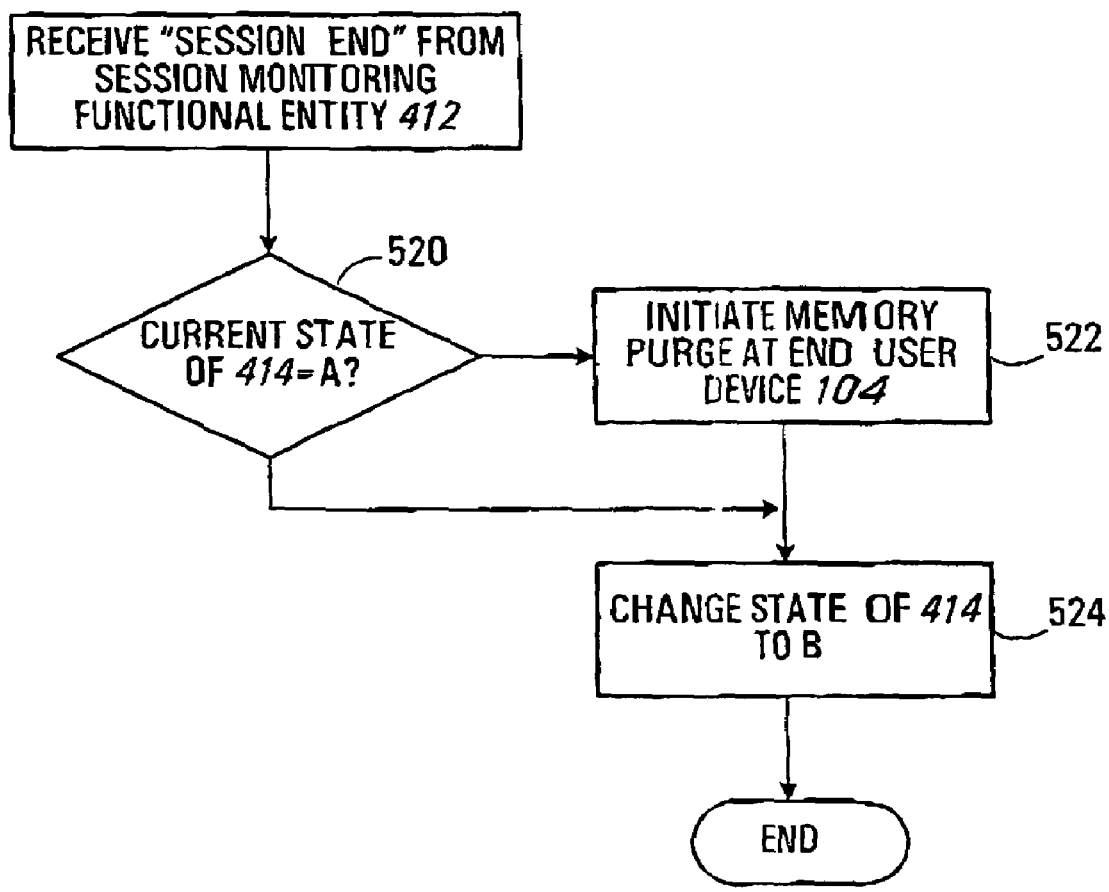

With reference to FIG. 5B, there is provided a flowchart illustrating operation of the control entity 410 in response to receipt of a "SESSION_END" message. At step 520, the control entity 410 checks whether the end user device 104 is involved in an ongoing non-healthcare session. This will be the case when the data switch 414 is in state "A". If this is indeed the case, then at step 522, the control entity 410 sends a message via link 440 in order to cause the end user device 104 to purge its memory store 212 of data loaded during the non-healthcare session. In addition, an optional message is sent to an entity in the host 100 (e.g., the PVR 406") to cause archiving/context-saving of the end user device 104 conditions, should the session being terminated need to be resurrected. Termination of the non-healthcare session is completed by causing the data switch 414 to enter state "B" (at step 524). Of course, it is noted that the order of execution of steps 522 and 524 may be reversed or they may even be performed simultaneously. It is also noted that termination of a healthcare session does not necessarily require the control entity 410 to cause the end user device to purge its memory store 212, as it is assumed that malicious software was not downloaded during the healthcare session. Nevertheless, there may still exist a desire to preserve confidentiality of the data in the memory store 212, and thus, the termination of a healthcare session may trigger other actions to preserve confidentiality of sensitive data in the end user device 104, up to and including a total volatile (writable) memory purge, which guarantees that no data from the healthcare session can be carried over into the non-healthcare session. For more details regarding procedures of this nature, the reader is referred to the U.S. patent application Ser. No. 10/813,358 entitled "Systems And Methods For Preserving Confidentiality Of Healthcare Information In A Point-Of-Care Communications Environment" to Graves et al., filed Mar. 31, 2004, incorporated by reference herein.

Figure 5C:
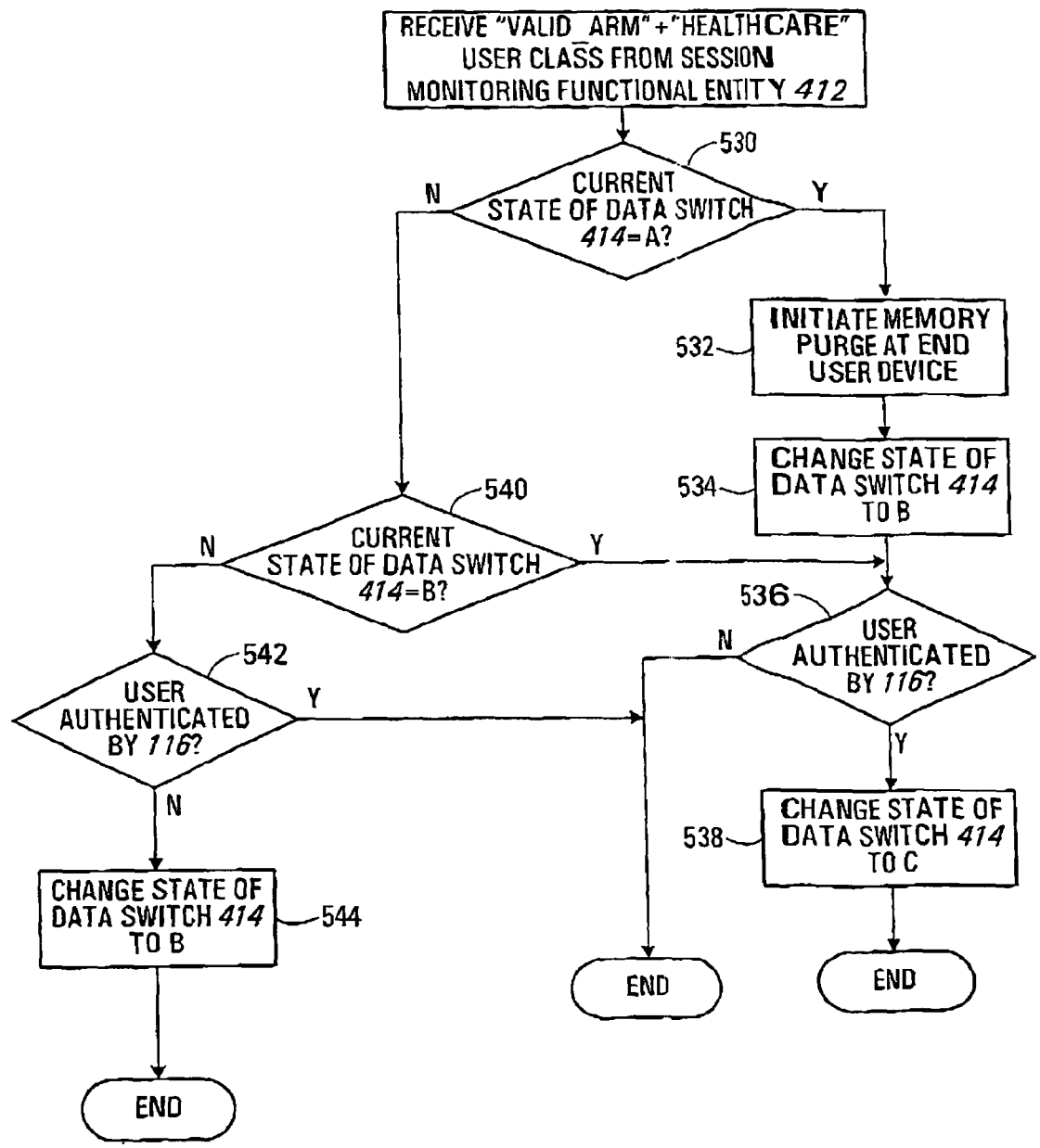

With reference now to FIG. 5C, there is provided a flowchart illustrating operation of the control entity 410 in response to receipt of a "VALID_ARM" message and in the case where the user class associated with the valid (but as yet unauthenticated) authentication request message is the healthcare user class. At step 530, the control entity 410 checks whether the end user device 104 is involved in an ongoing non-healthcare session. This will be the case when the data switch 414 is in state "A". If this is indeed the case, then at step 532, the control entity 410 sends a message via link 440 in order to cause the end user device 104 to purge its memory store 212 of data loaded during the ongoing non-healthcare session. In addition, an optional message is sent to an entity in the host 100 (e.g., the PVR 406") to cause archiving/context-saving of the end user device 104 conditions, should the session being terminated need to be resurrected. The control entity 410 then proceeds to step 534, where it sends a message to the data switch 414 along link 450, causing the data switch 414 to enter state "B". It is noted that the order of execution of steps 532 and 534 may be reversed or these steps may even be performed simultaneously. Next, the control entity 410 waits until it receives an indication as to whether authentication of the healthcare user was successful or unsuccessful (step 536). Authentication can be performed in many ways, including but not limited to those described in the U.S. patent application Ser. No. 10/813,230 entitled "Integrated And Secure Architecture For Delivery Of Communications Services In A Hospital" to Graves et al., filed Mar. 31, 2004, incorporated by reference herein. If authentication was successful, the control entity 410 changes the state of the data switch 414 to state "C" (step 538) in order to begin supporting a healthcare session between the end user device 104 and the routing entity 112B. If authentication was unsuccessful, then since the data switch 414 is already in state "B", no specific further action is required. It is also within the scope of the present invention to execute step 534 at this point rather than earlier.

If, however, step 530 reveals that the end user device 104 is not involved in an ongoing non-healthcare session, then the control entity 410 proceeds to step 540, where it checks whether the end user device is not involved in either an ongoing healthcare session or an ongoing non-healthcare session (i.e., if the data switch is in state "B"). If this is true, then the control entity returns to step 536, where the control entity 410 waits until it receives an indication as to whether authentication of the healthcare user was successful or unsuccessful. On the other hand, if steps 530 and 540 reveal that the end user device 104 is involved in an ongoing healthcare session, this means that the data switch 414 is in state C. The control entity 410 then proceeds to step 542, where the control entity 410 waits until it receives an indication as to whether authentication of the healthcare user was successful or unsuccessful. If authentication was successful, no specific further action is required since the data switch 414 was already in state C. If authentication was unsuccessful, then the control entity 410 proceeds to step 544 in order to set the data switch 414 to state "B" and terminate communication with the end user device 104.

Figure 5D:
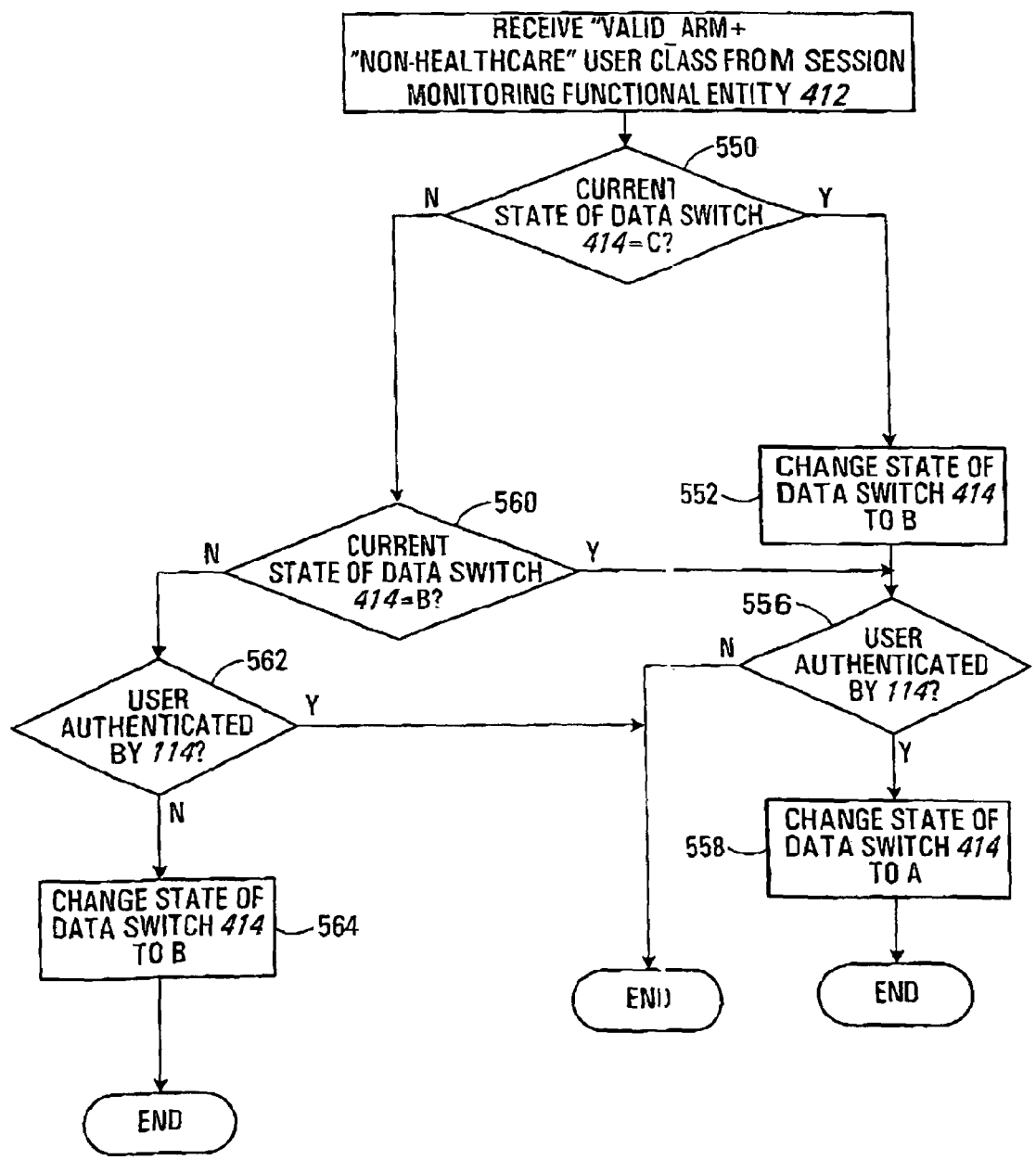

With reference now to FIG. 5D, there is provided a flowchart illustrating operation of the control entity 410 in response to receipt of a "VALID_ARM" message and in the case where the user class associated with the valid (but as yet unauthenticated) authentication request message is the non-healthcare user class. At step 550, the control entity 410 checks whether the end user device 104 is involved in an ongoing healthcare session. This will be the case when the data switch 414 is in state "C". If this is indeed the case, the control entity 410 proceeds to step 552, where it sends a message to the data switch 414 along link 450, causing the data switch 414 to enter state "B". Next, the control entity 410 waits until it receives an indication as to whether authentication of the non-healthcare user was successful or unsuccessful (step 556). Authentication can be performed in many ways, including but not limited to those described in the U.S. patent application Ser. No. 10/813,230 entitled "Integrated And Secure Architecture For Delivery Of Communications Services In A Hospital" to Graves et al., filed Mar. 31, 2004, incorporated by reference herein. If authentication was successful, the control entity 410 changes the state of the data switch 414 to state "A" (step 558) in order to begin supporting a non-healthcare session between the end user device 104 and the routing entity 112A. If authentication was unsuccessful, then since the data switch 414 is already in state "B", no specific further action is required.

It is noted that subsequent to an affirmative decision in step 520, it was not necessary to send a message via link 440 in order to cause the end user device 104 to purge its memory store 212 of data loaded during the ongoing healthcare session. Nevertheless, there may exist a desire to either delete the data in the memory store 212 or preserve its confidentiality, and thus, the receipt of an authentication request message from a non-healthcare user during a healthcare session may trigger a memory purge or other actions to preserve confidentiality of sensitive data in the end user device 104. For more details regarding procedures of this nature, the reader is referred to the U.S. patent application Ser. No. 10/813,358 entitled "Systems And Methods For Preserving Confidentiality Of Healthcare Information In A Point-Of-Care Communications Environment" to Graves et al., filed Mar. 31, 2004, incorporated by reference herein. In addition, an optional message may be sent to an entity in the host 100 (e.g., the PVR 406") to cause archiving/context-saving of the end user device 104 conditions, should the session being terminated need to be resurrected.

Returning now to the case where step 550 reveals that the end user device 104 is not involved in an ongoing healthcare session, the control entity 410 proceeds to step 560, where it checks whether the end user device is not involved in either an ongoing healthcare session or an ongoing non-healthcare session (i.e., if the data switch is in state "B"). If this is true, then the control entity returns to step 556, where the control entity 410 waits until it receives an indication as to whether authentication of the non-healthcare user was successful or unsuccessful. On the other hand, if steps 550 and 560 reveal that the end user device 104 is involved in an ongoing non-healthcare session, this means that the data switch 414 is in state A. The control entity 410 then proceeds to step 562, where the control entity 410 waits until it receives an indication as to whether authentication of the non-healthcare user was successful or unsuccessful. If authentication was successful, no specific further action is required since the data switch 414 was already in state A. If authentication was unsuccessful, then the control entity 410 proceeds to step 564 in order to set the data switch 414 to state "B" and terminate communication with the end user device 104.

EXAMPLE

Figure 6A:
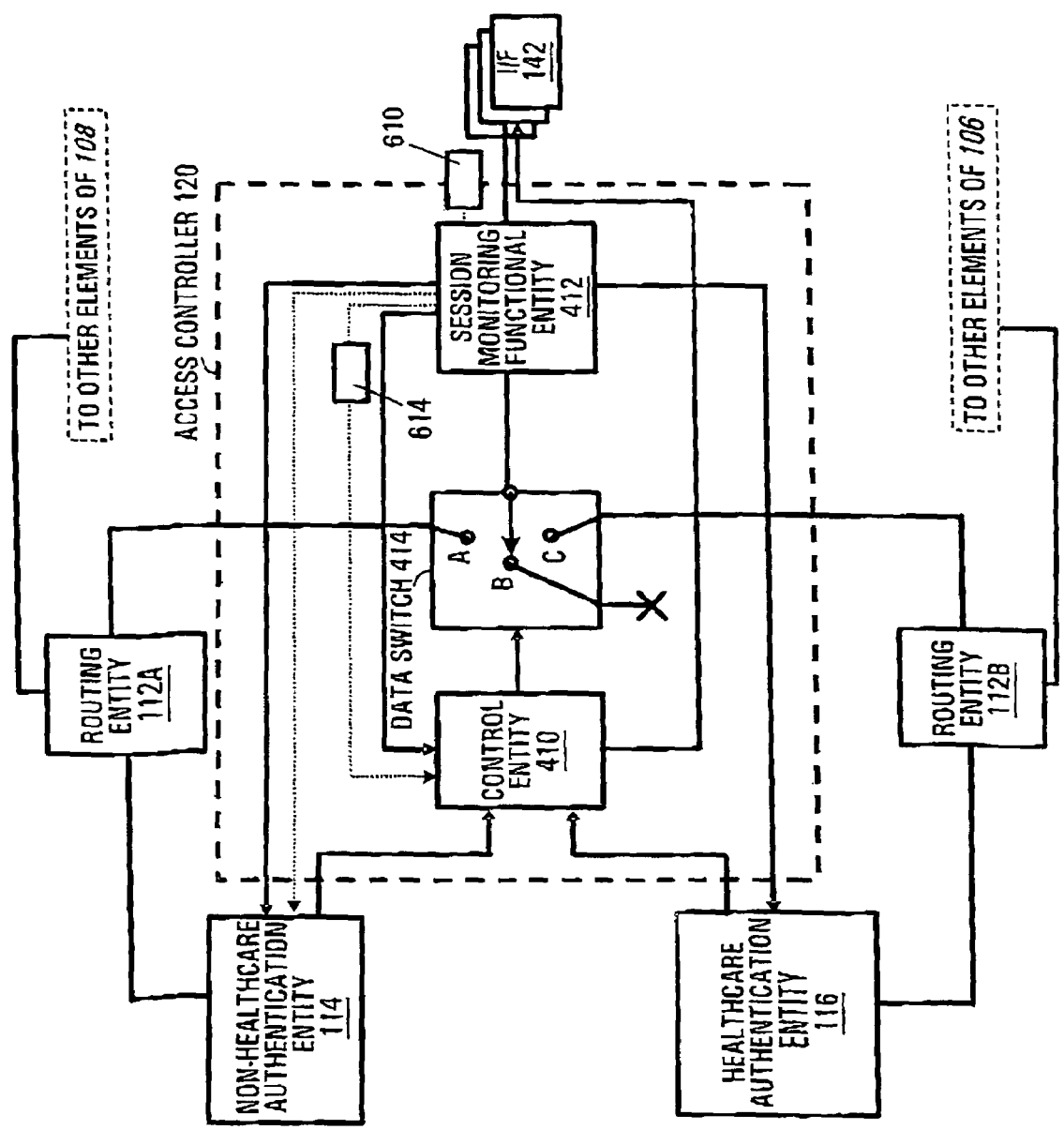
FIGS. 6A-6G illustrate steps in a procedure whereby establishment of a session with a non-healthcare user is followed by establishment of a session with a healthcare user.

An example of operation of the control entity 410, the data switch 414 and the session monitoring functional entity 412 will now be described with reference to an example and in conjunction with FIGS. 6A-6G. In FIG. 6A, it is assumed that the data switch 414 is in state "B", i.e., there is no ongoing session between the end user device and either the healthcare data processing resources 106 or the non-healthcare data processing resources 108. An authentication request message 610 is received at the session monitoring functional entity 412 from the end user device 104 via the interface 142. The session monitoring functional entity 412 detects the authentication request message 610 (steps 502, 504, 508) and validates it (step 510), realizing that it is associated with a non-healthcare user, such as a patient. The session monitoring functional entity 412 then sends the authentication request message 610 to the non-healthcare authentication entity 114 for authentication purposes and also sends a "VALID_ARM" message 614, as well as an identification of the non-healthcare user class, to the control entity 410 (step 512). The control entity 410 thus executes steps 550 and 560, and awaits the results of authentication at step 556.

Figure 6B:
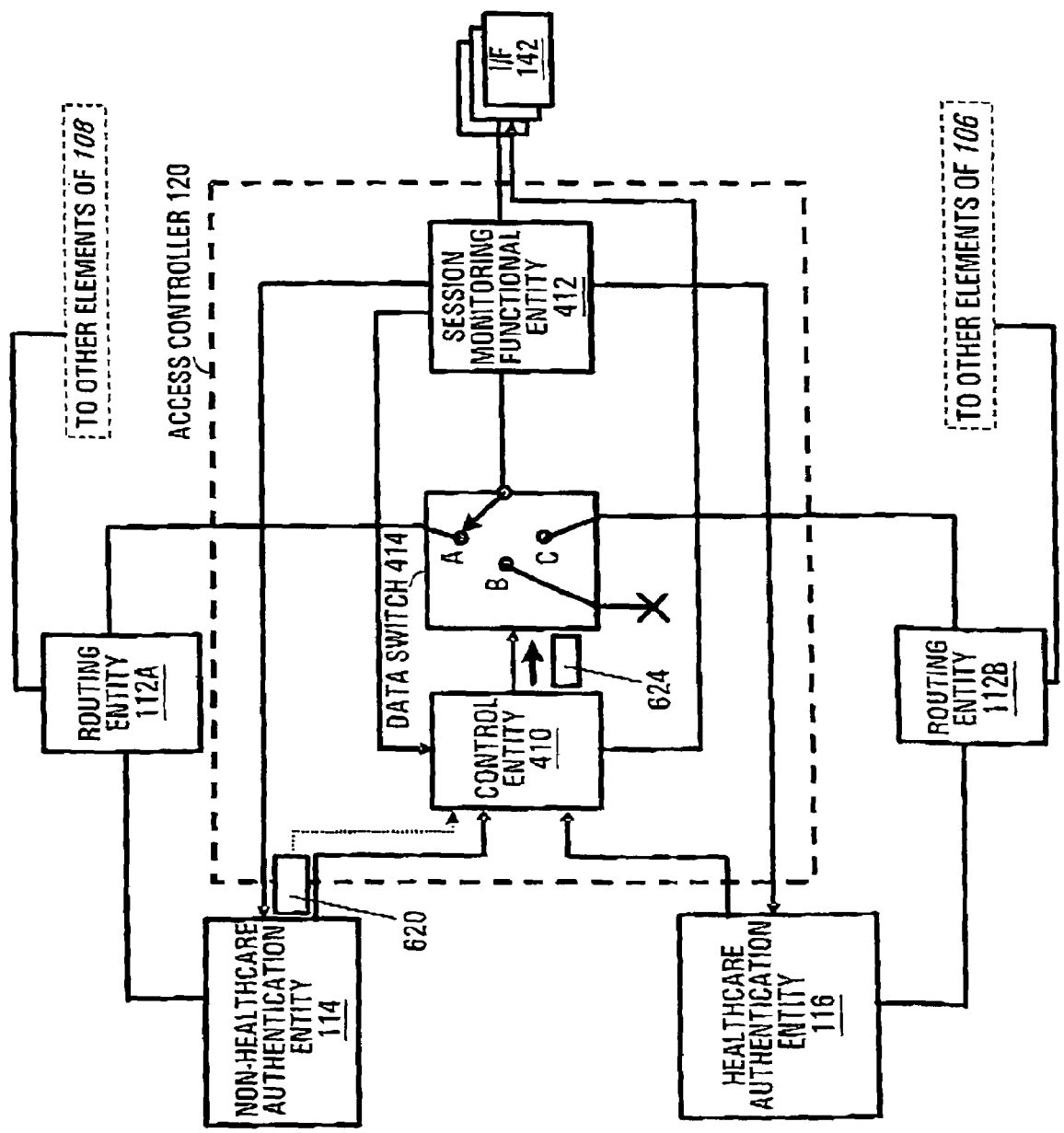
Figure 6C:
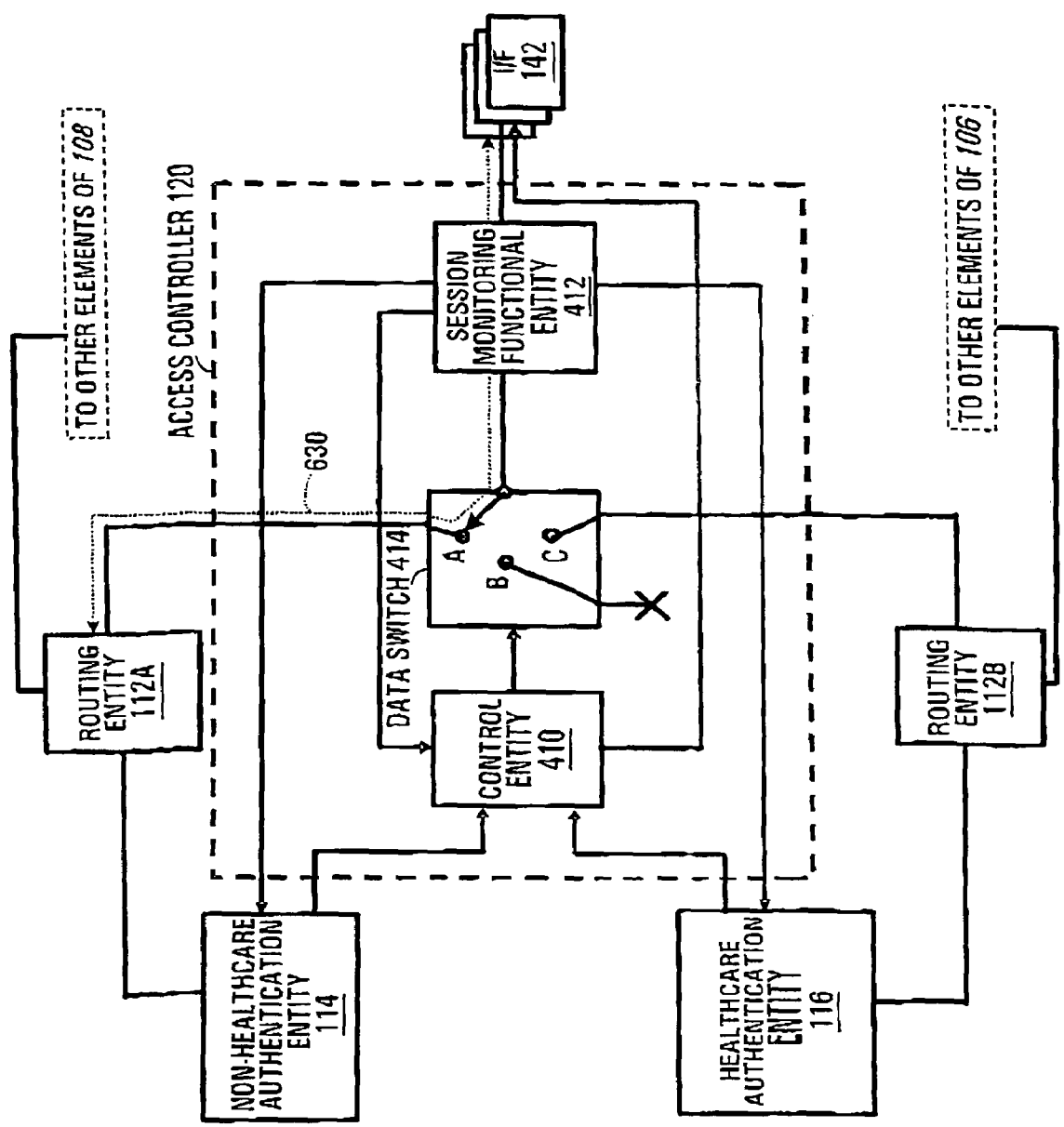

In FIG. 6B, the non-healthcare authentication entity 114 performs authentication in one of a variety of suitable ways. For example, if stored corroborating evidence stored in the non-healthcare AAA database 164 corresponding to the user identity matches the corroborating evidence supplied by the user by way of the authentication request message 610, then the authentication is said to have been successful. It is assumed that authentication of the non-healthcare user has been successful. This fact is communicated to the control entity 410 in the form of a message 620. The control entity 410 thus executes step 556 where the "Y" branch is chosen, leading to step 558 where the control entity 410 sends a signal to the data switch 414 instructing it to operate in state "A". Upon switching into state "A", and with reference to FIG. 6C, a communication path 630 is established between the interface 142 and the routing entity 112A, which supports a session between the end user device 104 and the non-healthcare data processing resources 108.

During the non-healthcare session, the user of the end user device 104 may attempt to infiltrate the healthcare data processing resources in a variety of ways. In one case, the user may attempt to download malicious software directly from the Internet into one of the application servers 144A, . . . , 144N. The user may similarly wish to initiate a denial-of-service attack on the healthcare data processing resources 106. However, the data switch 414 is configured so as to prevent the non-healthcare data processing resources 108 from accessing the healthcare data processing resources 106. This protection can be achieved in hardware or in software. In another instance, the user may attempt to download spyware or other malicious terminal-compatible software into the end user terminal 104, despite the limited capabilities of an end user device 104 implemented as a thin client terminal. This is not prevented per se by the data switch 414. However, the operation of the access controller 120 is such that termination of the non-healthcare session will leave the end user device 104 incapable of initiating an attack on the healthcare data processing resources 106. This will now be described in greater detail.

Figure 6D:
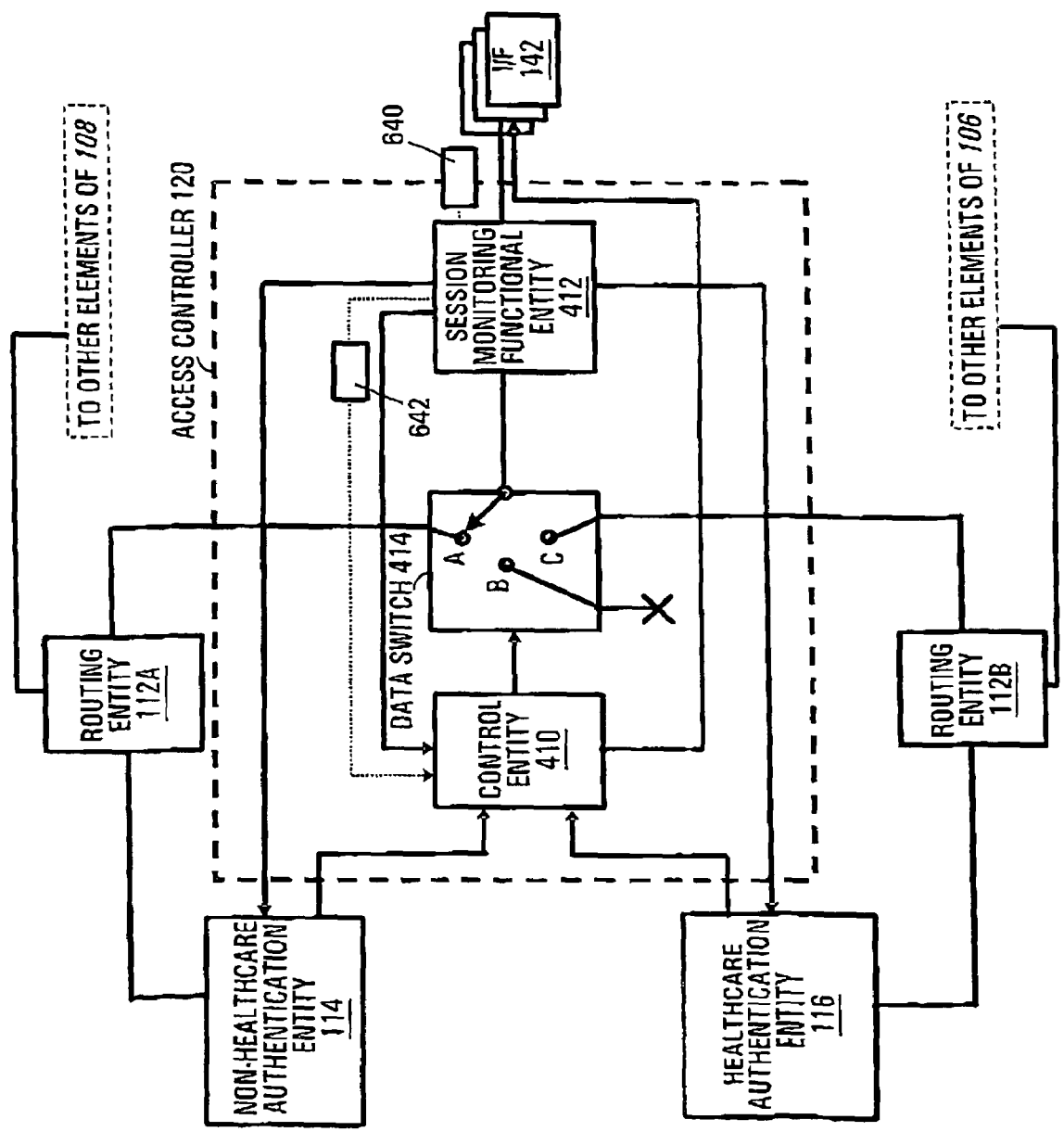

Specifically, with reference to FIG. 6D, it is assumed that before termination of the non-healthcare session, a healthcare user (whether legitimate or whose credentials have been spoofed) is desirous of accessing the healthcare data processing resources 106. In this case, a new authentication request message 640 is received at the session monitoring functional entity 412 from the interface 142. Again, the session monitoring functional entity 412 detects the authentication request message 640 (steps 502, 504, 508) and validates it (step 510), realizing that it is associated with a user purported to be a healthcare user. The session monitoring functional entity 412 then sends a "VALID_ARM" message 642, as well as an identification of the healthcare user class, to the control entity 410 (step 512).

Figure 6E:
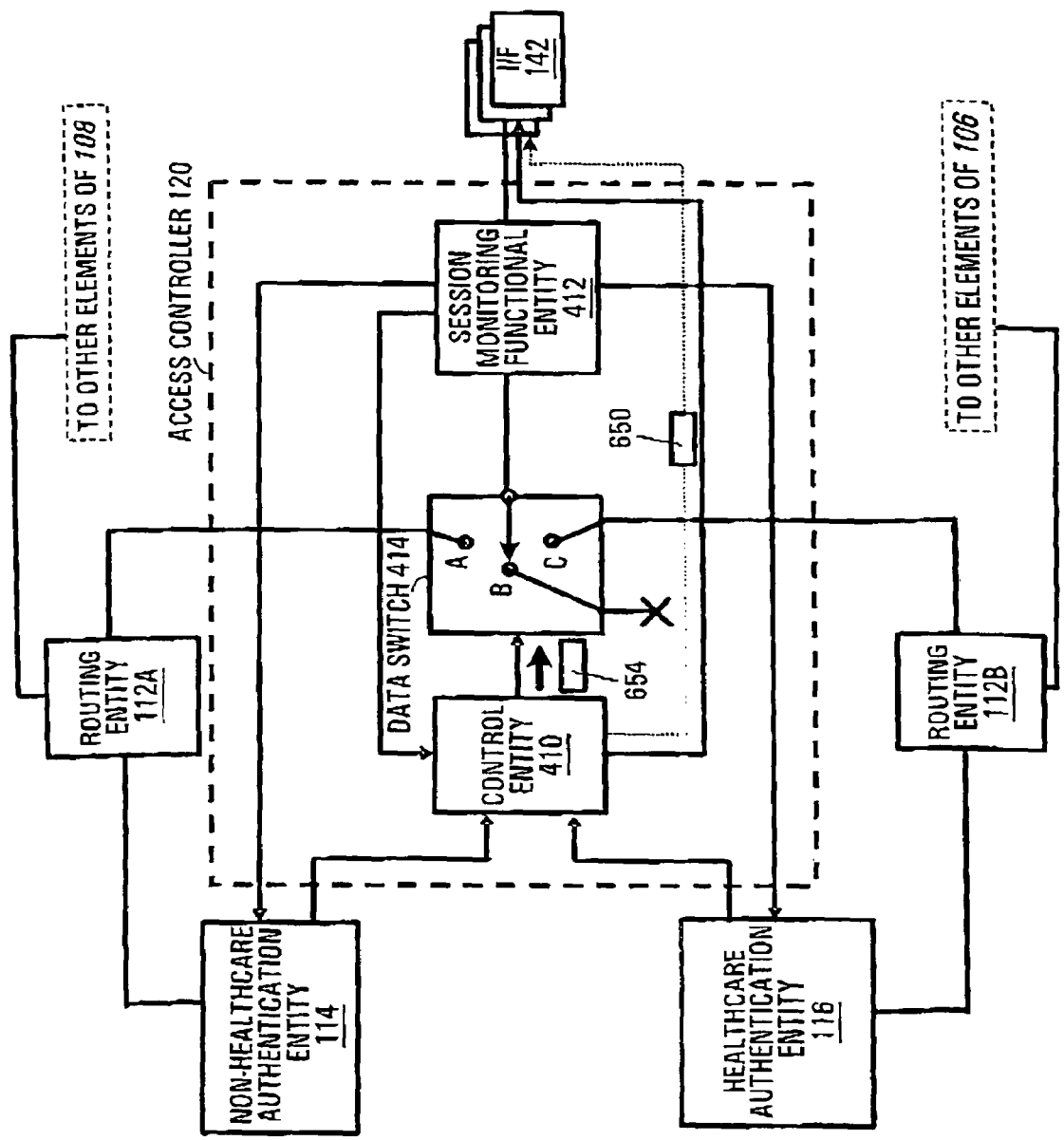
Figure 6F:
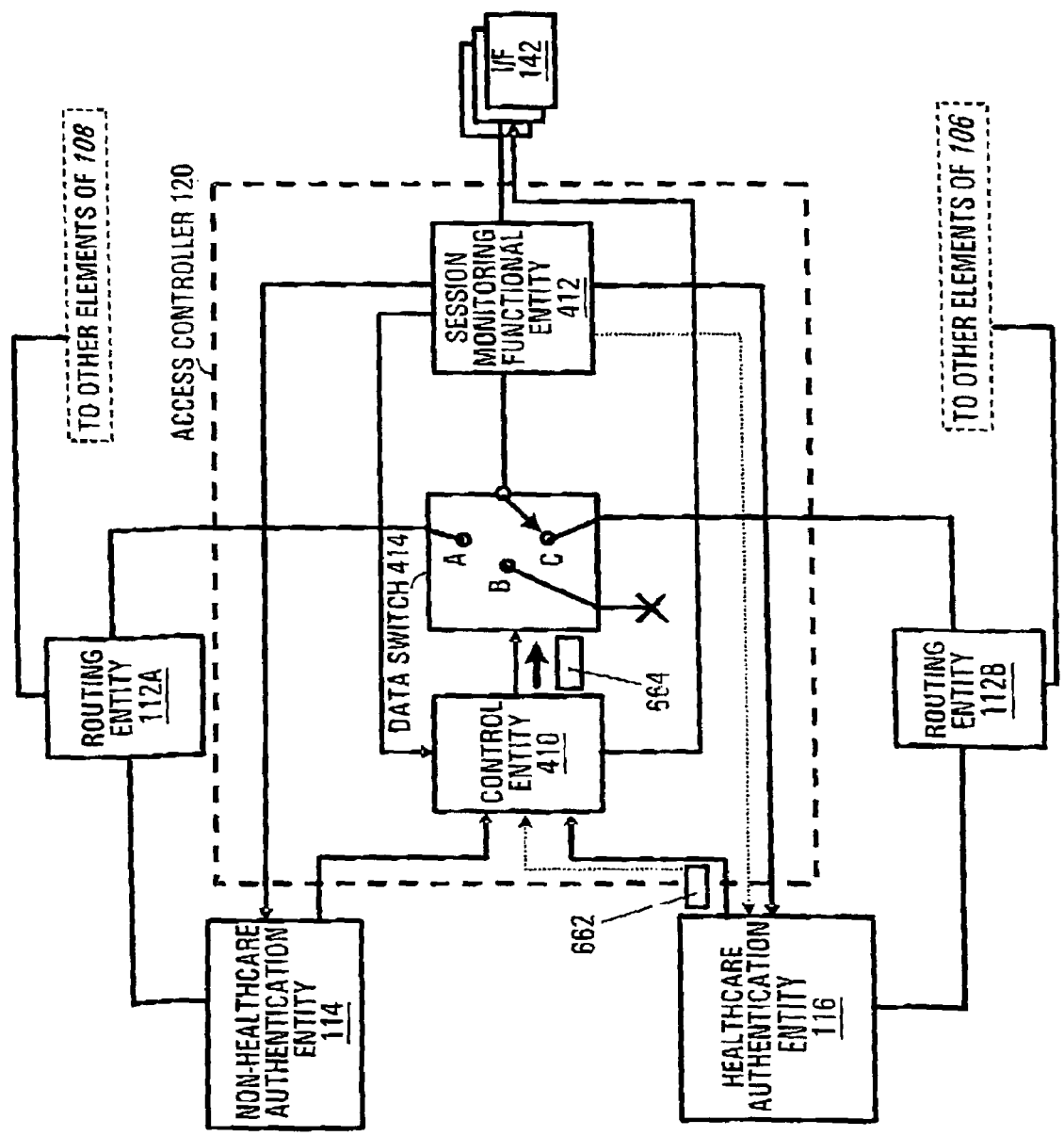
Figure 6G:
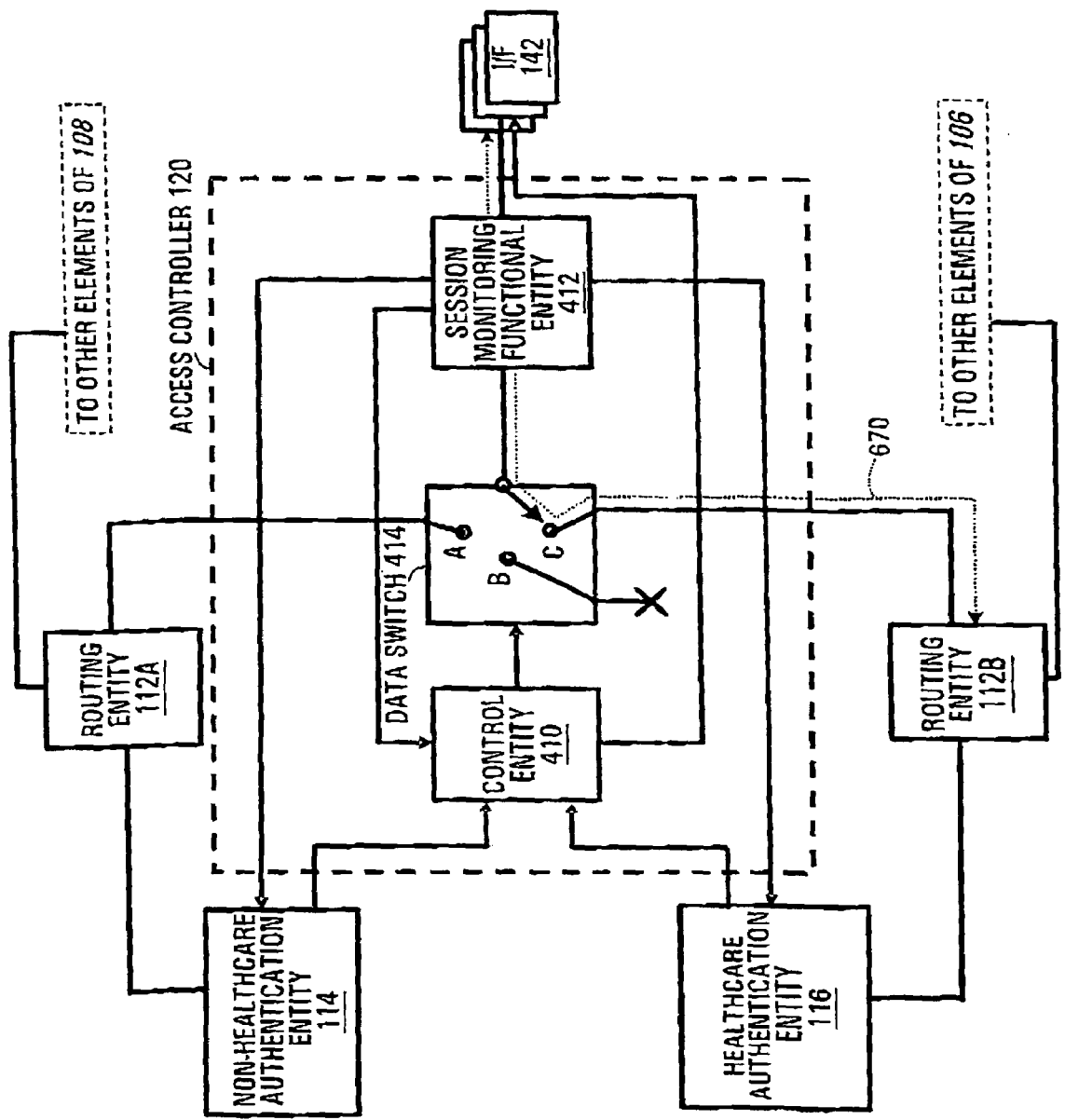

At this point, and with reference to FIG. 6E, the control entity 410 is programmed to initiate a memory purge by the end user device 104 (steps 530 and 532). This is achieved by sending a message 650 to the end user device via the interface 142. Once at the end user device 104 (see FIG. 2), the message 650 reaches the network interface 208, which forwards the message 650 to the memory store 212 along the memory purge line 302. The memory store 212 takes action by purging data that it has loaded during the previous non-healthcare session. This may include partial or complete erasure of certain predetermined portions of the memory store 212, for example. Thus, any malicious software downloaded by the non-healthcare user during the previous session is obliterated, which prevents potential future corruption of the healthcare data processing resources 106. In addition, an optional message is sent to an entity in the host 100 (e.g., the PVR 406") to cause archiving/context-saving of the end user device 104 conditions, should the session being terminated need to be resurrected.

Continuing with the actions taken by the control entity 410, the latter will then proceed to instruct the data switch 414 to enter state "B" (step 534), and then will arrive at step 536, where the results of authentication are awaited. Meanwhile, with reference to FIG. 6F, and still as part of step 512, the session monitoring functional entity 412 sends the authentication request message 640 to the healthcare authentication entity 116 for authentication purposes. The healthcare authentication entity 116 performs authentication in one of a variety of suitable ways. For example, if stored corroborating evidence stored in the healthcare AAA database 162 corresponding to the user identity matches the corroborating evidence supplied by the user by way of the authentication request message 640, then the authentication is said to have been successful. It is assumed that authentication of the new healthcare user has been successful. This fact is communicated to the control entity 410 in the form of a message 662. The control entity 410 thus executes step 536 where the "Y" branch is chosen, leading to step 538 where the control entity 410 sends a signal to the data switch 414 instructing it to operate in state "C". Upon switching into state "C", and with reference to FIG. 6G, a communication path 670 is established between the interface 142 and the routing entity 112B, which supports a session between the end user device 104 and the healthcare data processing resources 106.

Those skilled in the art will appreciate that in some embodiments, the functionality of the control entity 410, session monitoring functional entity 412 and the data switch 414 may be implemented as pre-programmed hardware or firmware elements (e.g., application specific integrated circuits (ASICs), electrically erasable programmable read-only memories (EEPROMs), etc.), or other related components. In other embodiments, the control entity 410, session monitoring functional entity 412 and the data switch 414 may be implemented as an arithmetic and logic unit (ALU) having access to a code memory (not shown) which stores program instructions for the operation of the ALU. The program instructions could be stored on a medium which is fixed, tangible and readable directly by the control entity 410, session monitoring functional entity 412 and the data switch 414, (e.g., removable diskette, CD-ROM, ROM, or fixed disk), or the program instructions could be stored remotely but transmittable to the control entity 410, session monitoring functional entity 412 and the data switch 414 via a modem or other interface device (e.g., a communications adapter) connected to a network over a transmission medium. The transmission medium may be either a tangible medium (e.g., optical or analog communications lines) or a medium implemented using wireless techniques (e.g., microwave, infrared or other transmission schemes).

While specific embodiments of the present invention have been described and illustrated, it will be apparent to those skilled in the art that numerous modifications and variations can be made without departing from the scope of the invention as defined in the appended claims.

What is claimed is:

1. A system comprising;
   healthcare data processing resources;
   non-healthcare data processing resources;
   a switching entity disposed between the healthcare data processing resources and the non-healthcare data processing resources;
   a communication link connected to the switching entity and connectable to an end user device;
   a healthcare authentication entity for authenticating users claiming to be healthcare users and a non-healthcare authentication entity for authenticating users claiming to be non-healthcare users;
   the switching entity being operative to alternatively support, over the communication link, either a healthcare session between the end user device and the healthcare data processing resources, or a non-healthcare session between the end user device and the non-healthcare data processing resources;
   the switching entity being configured to prevent the healthcare data processing resources and the non-healthcare data processing resources from communicating with each other via the switching entity.

2. The system defined in claim 1, wherein the switching entity is capable of operation in a first state in which the end user device is communicatively coupled to the healthcare data processing resources to support a healthcare session and a second state in which the end user device is communicatively coupled to the non-healthcare data processing resources to support a non-healthcare session.

3. The system defined in claim 2, further comprising a control entity for controlling the state in which the switching entity operates.

4. The system defined in claim 3, further comprising a session monitoring functional entity operative to:
   receive an authentication request message from a user along the communication link;
   determine, from the authentication request message, whether the user is claiming to be a healthcare user or a non-healthcare user;
   send the authentication request message to a selected one of the healthcare authentication entity and the non-healthcare authentication entity in dependence upon whether it has been determined that the user is claiming to be a healthcare user or a non-healthcare user.

5. The system defined in claim 4, the session monitoring functional entity being further operative to send to the control entity an indication of the selected authentication entity.

6. The system defined in claim 5, each of the healthcare authentication entity and the non-healthcare authentication entity being operative to send to the control entity an indication of successful or unsuccessful authentication.

7. The system defined in claim 6, the control entity having an operation defined by:
   responsive to successful authentication by the healthcare authentication entity, causing the switching entity to operate in the first state.

8. The system defined in claim 7, the control entity having an operation further defined by:
   responsive to successful authentication by the non-healthcare authentication entity, causing the switching entity to operate in the second state.

9. The system defined in claim 6, the control entity having an operation defined by:
   if the authentication request message is received while the switching entity is operating in the first state, and the selected authentication entity is the non-healthcare authentication entity, then responsive to successful authentication by the non-healthcare authentication entity, causing the switching entity to operate in the second state.

10. The system defined in claim 9, the control entity having an operation defined by:
    if the authentication request message is received while the switching entity is operating in the second state, and the selected authentication entity is the healthcare authentication entity, then responsive to successful authentication by the healthcare authentication entity, causing the switching entity to operate in the first state.

11. The system defined in claim 10, wherein the switching entity is implemented in hardware.

12. The system defined in claim 10, wherein the switching entity is implemented in software.

13. The system defined in claim 6, the control entity having an operation defined by:
    if the authentication request message is received while the switching entity is operating in the second state and a particular non-healthcare session is in progress, and the selected authentication entity is the healthcare authentication entity, initiating a memory purge at the end user device.

14. The system defined in claim 13, the control entity having an operation further defined by:
    if the authentication request message is received while the switching entity is operating in the second state and a particular non-healthcare session is in progress, and the selected authentication entity is the healthcare authentication entity, initiating a context saving operation by the non-healthcare data processing resources.

15. The system defined in claim 13, the control entity having an operation further defined by:
    subsequent to initiating a memory purge at the end user device, and responsive to successful authentication by the healthcare authentication entity, causing the switching entity to operate in the first state.

16. The system defined in claim 15, the control entity having an operation further defined by:
    responsive to successful authentication by the non-healthcare authentication entity, causing the switching entity to operate in the second state.

17. The system defined in claim 13, wherein initiating a memory purge at the end user device comprises:
    releasing a command towards the end user device to cause the end user device to purge data loaded into the end user device during the particular non-healthcare session.

18. The system defined in claim 13, wherein initiating a memory purge at the end user device comprises:

releasing a command towards the end user device to cause the end user device to purge all data loaded into the end user device during the particular non-healthcare session.

19. The system defined in claim 6, the session monitoring functional entity being operative to:
receive a message indicative of termination of an ongoing session;
send to the control entity a second message indicative of termination of the session.

20. The system defined in claim 19, the control entity being operative to respond to receipt of the second message to initiate a memory purge at the end user device.

21. The system defined in claim 20, wherein initiating a memory purge at the end user device comprises:
releasing a command towards the end user device to cause the end user device to purge data loaded into the end user device during the terminated session.

22. The system defined in claim 4, the session monitoring functional entity being operative to:
receive a message indicative of termination of an ongoing session;
send to the control entity a second message indicative of termination of the session.

23. The system defined in claim 22, the control entity being operative to respond to receipt of the second message to initiate a memory purge at the end user device.

24. The system defined in claim 23, wherein initiating a memory purge at the end user device comprises:
releasing a command towards the end user device to cause the end user device to purge data loaded into the end user device during the terminated session.

25. The system defined in claim 3, further comprising a session monitoring functional entity operative to:
receive a message indicative of termination of an ongoing session;
send to the control entity a second message indicative of termination of the session.

26. The system defined in claim 25, the control entity being operative to respond to receipt of the second message to initiate a memory purge at the end user device.

27. The system defined in claim 26, wherein initiating a memory purge at the end user device comprises:
releasing a command towards the end user device to cause the end user device to purge data loaded into the end user device during the terminated session.

28. The system defined in claim 1, wherein the healthcare data processing resources comprise a plurality of healthcare application servers for running clinical software.

29. The system defined in claim 1, wherein the healthcare session allows the delivery of a computerized physician order entry service.

30. The system defined in claim 1, wherein the non-healthcare data processing resources comprise a digital entertainment head end for controlling delivery to the end user device of received digital entertainment services.

31. The system defined in claim 30, wherein the non-healthcare session allows the delivery of patient entertainment services.

32. The system defined in claim 30, wherein the non-healthcare session allows the delivery of personal video recorder services.

33. The system defined in claim 1, wherein the non-healthcare data processing resources comprise an Internet gateway.

34. The system defined in claim 1, wherein the non-healthcare data processing resources comprise a patient information server for allowing access to patient information services.

35. The system defined in claim 1, wherein each healthcare session and each non-healthcare session is implemented as a virtual connection.

36. A system comprising:
healthcare data processing resources, the healthcare data processing resources comprising a plurality of healthcare application servers for running clinical software;
non-healthcare data processing resources;
a switching entity disposed between the healthcare data processing resources and the non-healthcare data processing resources;
a communication link connected to the switching entity and connectable to an end user device;
the switching entity being operative to alternatively support, over the communication link, either a healthcare session between the end user device and the healthcare data processing resources, or a non-healthcare session between the end user device and the non-healthcare data processing resources, wherein the healthcare session allows the delivery of a computerized physician order entry service;
the switching entity being configured to prevent the healthcare data processing resources and the non-healthcare data processing resources from communicating with each other via the switching entity.

37. The system defined in claim 36, wherein the non-healthcare data processing resources comprise a digital entertainment head end for controlling delivery to the end user device of received digital entertainment services.

38. The system defined in claim 37, wherein the non-healthcare session allows the delivery of patient entertainment services.

39. The system defined in claim 37, wherein the non-healthcare session allows the delivery of personal video recorder services.

40. The system defined in claim 36, wherein the non-healthcare data processing resources comprise an Internet gateway.

41. The system defined in claim 36, wherein the non-healthcare data processing resources comprise a patient information server for allowing access to patient information services.

42. The system defined in claim 1, wherein the communication link is at least partly wireless.

43. The system defined in claim 1, wherein the communication link is at least partly fixed-wire.

44. The system defined in claim 1, wherein the communication link comprises point-to-point telephony wiring.

45. The system defined in claim 36, comprising a healthcare authentication entity for authenticating users claiming to be healthcare users and a non-healthcare authentication entity for authenticating users claiming to be non-healthcare users.

46. The system defined in claim 45, wherein the switching entity is capable of operation in a first state in which the end user device is communicatively coupled to the healthcare data processing resources to support a healthcare session and a second state in which the end user device is communicatively coupled to the non-healthcare data processing resources to support a non-healthcare session.

47. The system defined in claim 46, further comprising a control entity for controlling the state in which the switching entity operates.

48. The system defined in claim 47, further comprising a session monitoring functional entity operative to:
- receive an authentication request message from a user along the communication link;
- determine, from the authentication request message, whether the user is claiming to be a healthcare user or a non-healthcare user;
- send the authentication request message to a selected one of the healthcare authentication entity and the non-healthcare authentication entity in dependence upon whether it has been determined that the user is claiming to be a healthcare user or a non-healthcare user.

49. The system defined in claim 48, the session monitoring functional entity being further operative to send to the control entity an indication of the selected authentication entity.

50. The system defined in claim 49, each of the healthcare authentication entity and the non-healthcare authentication entity being operative to send to the control entity an indication of successful or unsuccessful authentication.

51. The system defined in claim 50, the control entity having an operation defined by:
- responsive to successful authentication by the healthcare authentication entity, causing the switching entity to operate in the first state.

52. The system defined in claim 50, the control entity having an operation further defined by:
- responsive to successful authentication by the non-healthcare authentication entity, causing the switching entity to operate in the second state.

53. The system defined in claim 50, the control entity having an operation defined by:
- if the authentication request message is received while the switching entity is operating in the first state, and the selected authentication entity is the non-healthcare authentication entity, then responsive to successful authentication by the non-healthcare authentication entity, causing the switching entity to operate in the second state.

54. The system defined in claim 50, the control entity having an operation defined by:
- if the authentication request message is received while the switching entity is operating in the second state, and the selected authentication entity is the healthcare authentication entity, then responsive to successful authentication by the healthcare authentication entity, causing the switching entity to operate in the first state.

55. The system defined in claim 50, the control entity having an operation defined by:
- if the authentication request message is received while the switching entity is operating in the second state and a particular non-healthcare session is in progress, and the selected authentication entity is the healthcare authentication entity, initiating a memory purge at the end user device.

56. The system defined in claim 55, the control entity having an operation further defined by:
- subsequent to initiating a memory purge at the end user device, and responsive to successful authentication by the healthcare authentication entity, causing the switching entity to operate in the first state.

57. The system defined in claim 56, the control entity having an operation further defined by:
- responsive to successful authentication by the non-healthcare authentication entity, causing the switching entity to operate in the second state.

58. The system defined in claim 55, wherein initiating a memory purge at the end user device comprises:
- releasing a command towards the end user device to cause the end user device to purge data loaded into the end user device during the particular non-healthcare session.

59. The system defined in claim 55, wherein initiating a memory purge at the end user device comprises:
- releasing a command towards the end user device to cause the end user device to purge all data loaded into the end user device during the particular non-healthcare session.

60. The system defined in claim 50, the control entity having an operation further defined by:
- if the authentication request message is received while the switching entity is operating in the second state and a particular non-healthcare session is in progress, and the selected authentication entity is the healthcare authentication entity, initiating a context saving operation by the non-healthcare data processing resources.

61. The system defined in claim 50, the session monitoring functional entity being operative to:
- receive a message indicative of termination of an ongoing session;
- send to the control entity a second message indicative of termination of the session.

62. The system defined in claim 61, the control entity being operative to respond to receipt of the second message to initiate a memory purge at the end user device.

63. The system defined in claim 62, wherein initiating a memory purge at the end user device comprises:
- releasing a command towards the end user device to cause the end user device to purge data loaded into the end user device during the terminated session.

64. The system defined in claim 48, the session monitoring functional entity being operative to:
- receive a message indicative of termination of an ongoing session;
- send to the control entity a second message indicative of termination of the session.

65. The system defined in claim 64, the control entity being operative to respond to receipt of the second message to initiate a memory purge at the end user device.

66. The system defined in claim 65, wherein initiating a memory purge at the end user device comprises:
- releasing a command towards the end user device to cause the end user device to purge data loaded into the end user device during the terminated session.

67. The system defined in claim 47, further comprising a session monitoring functional entity operative to:
- receive a message indicative of termination of an ongoing session;
- send to the control entity a second message indicative of termination of the session.

68. The system defined in claim 67, the control entity being operative to respond to receipt of the second message to initiate a memory purge at the end user device.

69. The system defined in claim 68, wherein initiating a memory purge at the end user device comprises:
- releasing a command towards the end user device to cause the end user device to purge data loaded into the end user device during the terminated session.

70. The system defined in claim 36, wherein the switching entity is implemented in hardware.

71. The system defined in claim 36, wherein the switching entity is implemented in software.

72. The system defined in claim 36, wherein the communication link is at least partly wireless.

73. The system defined in claim 36, wherein the communication link is at least partly fixed-wire.

74. The system defined in claim 36, wherein the communication link comprises point-to-point telephony wiring.

75. The system defined in claim 36, wherein each healthcare session and each non-healthcare session is implemented as a virtual connection.

* * * * *